(12) United States Patent
Fujii et al.

(10) Patent No.: US 11,484,564 B2
(45) Date of Patent: Nov. 1, 2022

(54) ADHESION PREVENTION MATERIAL

(71) Applicant: OTSUKA PHARMACEUTICAL FACTORY, INC., Naruto (JP)

(72) Inventors: Namiki Fujii, Naruto (JP); Yuichiro Yoshioka, Naruto (JP); Tatsuru Fukuda, Naruto (JP)

(73) Assignee: OTSUKA PHARMACEUTICAL FACTORY, INC., Naruto (JP)

(*) Notice: Subject to any disclaimer, the term of this patent is extended or adjusted under 35 U.S.C. 154(b) by 0 days.

(21) Appl. No.: 16/756,499

(22) PCT Filed: Oct. 19, 2018

(86) PCT No.: PCT/JP2018/038977
§ 371 (c)(1),
(2) Date: Apr. 16, 2020

(87) PCT Pub. No.: WO2019/078349
PCT Pub. Date: Apr. 25, 2019

(65) Prior Publication Data
US 2020/0282005 A1    Sep. 10, 2020

(30) Foreign Application Priority Data

Oct. 20, 2017 (JP) .............................. JP2017-204036
May 30, 2018 (JP) .............................. JP2018-103960

(51) Int. Cl.
| | |
|---|---|
| C07K 5/08 | (2006.01) |
| C07K 14/78 | (2006.01) |
| C07K 14/79 | (2006.01) |
| C07K 7/06 | (2006.01) |
| C07K 14/47 | (2006.01) |
| C07K 7/08 | (2006.01) |
| C07K 1/00 | (2006.01) |
| C07K 5/00 | (2006.01) |
| C07K 7/00 | (2006.01) |
| A61K 38/06 | (2006.01) |
| A61K 38/10 | (2006.01) |
| A61K 9/06 | (2006.01) |
| A61K 38/00 | (2006.01) |
| A61P 41/00 | (2006.01) |
| A61K 38/04 | (2006.01) |
| A61K 38/17 | (2006.01) |

(52) U.S. Cl.
CPC ............... *A61K 38/06* (2013.01); *A61K 9/06* (2013.01); *A61K 38/043* (2013.01); *A61K 38/10* (2013.01); *A61K 38/1709* (2013.01); *A61P 41/00* (2018.01)

(58) Field of Classification Search
CPC ........ C07K 5/08; C07K 14/78; C07K 14/605; C07K 14/79; C07K 1/1075; C07K 5/06165; C07K 5/0806; C07K 7/06; C07K 14/005; C07K 14/47; C07K 14/521; C07K 14/565; C07K 14/575; C07K 2319/00; C07K 2319/035; C07K 5/0804; C07K 5/0812; C07K 5/0823; C07K 7/08; C07K 1/00; C07K 5/00; C07K 5/087; C07K 5/097; C07K 7/00; A61K 38/043; A61K 38/06; A61K 38/10; A61K 38/1709; A61K 9/06; A61K 38/00; A61K 47/483; A61P 41/00; A61P 47/48
See application file for complete search history.

(56) References Cited

U.S. PATENT DOCUMENTS

| | | | |
|---|---|---|---|
| 5,399,361 A | 3/1995 | Song et al. | |
| 5,512,301 A | 4/1996 | Song et al. | |
| 8,076,294 B2 * | 12/2011 | Kinney | .................. C07K 14/78 514/17.2 |
| 2001/0016205 A1 | 8/2001 | Shimizu | |
| 2006/0041320 A1 | 2/2006 | Matsuda | |
| 2010/0021527 A1 * | 1/2010 | Yang | ....................... A61P 17/02 424/445 |

(Continued)

FOREIGN PATENT DOCUMENTS

| | | |
|---|---|---|
| EP | 0 686 402 A1 | 12/1995 |
| JP | 08-500334 A | 1/1996 |

(Continued)

OTHER PUBLICATIONS

International Search Report of PCT/JP2018/038977 dated Dec. 11, 2018 [PCT/ISA/210].

(Continued)

*Primary Examiner* — Julie Ha
(74) *Attorney, Agent, or Firm* — Sughrue Mion, PLLC

(57) ABSTRACT

The purpose of the present invention is to provide an adhesion prevention material capable of exhibiting excellent adhesion preventive effect. This adhesion prevention material concurrently uses: (A) a peptide (A-1) having an amino acid sequence-(X-Pro-Y)n-[wherein X represents an arbitrary defined amino acid, Pro represents proline, Y represents hydroxyproline or proline, and n is an integer between 1 and 10] and/or a peptide (A-2) having an amino acid sequence-(Pro-Y)m-[wherein Pro represents proline, Y represents hydroxyproline or proline, and m is an integer between 1-10]; and (B) a gelatin gel. This adhesion prevention material exhibits a dramatically enhanced adhesion preventive effect as compared with the case where the abovementioned components are used individually, and in particular, has a markedly superior effect against adhesion of tendons.

19 Claims, 23 Drawing Sheets

(56) References Cited

U.S. PATENT DOCUMENTS

| | | |
|---|---|---|
| 2010/0068342 A1 | 3/2010 | Matsumoto et al. |
| 2013/0116405 A1 | 5/2013 | Yu et al. |
| 2013/0137850 A1 | 5/2013 | Yoshimura et al. |
| 2014/0308365 A1 | 10/2014 | Fukuda et al. |

FOREIGN PATENT DOCUMENTS

| | | |
|---|---|---|
| JP | 08-052204 A | 2/1996 |
| JP | 09-103479 A | 4/1997 |
| JP | 10-113384 A | 5/1998 |
| JP | 2000-271207 A | 10/2000 |
| JP | 2004-065780 A | 3/2004 |
| JP | 2008284257 A | 11/2008 |
| JP | 2013-112653 A | 6/2013 |
| JP | 2013-223644 A | 10/2013 |
| WO | 98/22157 A1 | 5/1998 |
| WO | 2013/077414 A1 | 5/2013 |

OTHER PUBLICATIONS

Communication dated Aug. 5, 2021, from the European Patent Office in application No. 18869111.7.

* cited by examiner

| Test sample | Number of individuals still retaining/Total number of individuals |
|---|---|
| Comparative Example 8 | 0/9 |
| Example 8-1 | 8/8 |
| Example 8-2 | 6/6 |
| Example 8-3 | 7/7 |

| Test sample | Number of individuals still retaining test sample on flexor tendon/Total number of individuals |
|---|---|
| Comparative Example 11 | 0/10 |
| Example 11-1 | 9/9 |
| Example 11-2 | 6/6 |

Example 11-1

Comparative Example 11

Example 11-2

ADHESION PREVENTION MATERIAL

CROSS REFERENCE TO RELATED APPLICATIONS

This application is a National Stage of International Application No. PCT/JP2018/038977, filed Oct. 19, 2018, claiming priorities to Japanese Patent Application No. 2017-204036, filed Oct. 20, 2017 and Japanese Patent Application No. 2018-103960, filed May 30, 2018.

TECHNICAL FIELD

The present invention relates to an antiadhesive material having an excellent antiadhesive effect (especially, antiadhesive effect on tendon adhesion).

BACKGROUND ART

Adhesion refers to a condition in which organs or tissues that are originally located close to but separated from each other become continuous. Post-operational sutured-portion adhesion is one of the artificially occurring inflammatory adhesions, and is a frequently occurring complication associated with an operation with a varying degree. In particular, it is known that when tendon adhesion occurs after treatment of tendon injury, tendon rupture, bone fracture, or the like, a joint loses movability or the range of joint motion decreases. Thus, it is important for normal recovery of injured tissues to prevent tendon adhesion after a surgical operation by an antiadhesive material.

An antiadhesive material is administered to a site where prevention of adhesion is required. The antiadhesive material is required to stay on the site for a certain period of time and function as a physical barrier. In particular, when the antiadhesive material is used for preventing tendon adhesion, since tissues surrounding a tendon are minute and intricate, the antiadhesive material is required to have excellent diffusibility to spread over the target site after administration. Further, the antiadhesive material is required to stay on the target site for a certain period of time and function as a physical barrier after administration.

Conventionally, various antiadhesive materials have been investigated. For example, Patent Document 1 proposes a solid antiadhesive material containing a gelling agent, a salt of an organic acid and/or an inorganic acid with a divalent metal, and polyethylene glycol, in which the solid antiadhesive material is mixed with water before use and administered in liquid form, and the solid antiadhesive material becomes gel form after administration (see Patent Document 1). It is thought that an antiadhesive material which is administered in liquid form and becomes gel form after administration as described above is effective for preventing tendon adhesion even when applied to a minute and intricate tissue because the antiadhesive material can diffuse and spread over the applied tissue and can exert a physical barrier function.

In addition, antiadhesive materials using a collagen-like peptide or gelatin have been also proposed. For example, Patent Document 2 discloses that a condensation polymer of a collagen-like peptide oligomer including -(Pro-Y-Gly)$_n$-[Y is Pro or Hyp, and n is an integer of 1 or more] and a polysaccharide can be used as an antiadhesive material. Further, Patent Document 3 discloses that a biomedical material in which gelatin is crosslinked with a succinimide-modified poly-L-glutamic acid can be used as an antiadhesive material.

However, with respect to an antiadhesive material, there has been an increasing demand for an improved function and convenience in use, and it is desired to develop a new antiadhesive material. In particular, it is desired to develop a new antiadhesive material which can exert both high levels of diffusibility into a target site and a physical barrier function for a certain period of time, and is preferably applicable to a tendon.

PRIOR ART DOCUMENTS

Patent Documents

Patent Document 1: International Patent Application Publication No. 2013/77414
Patent Document 2: Japanese Patent Laid-open Publication No. 2013-112653
Patent Document 3: Japanese Patent Laid-open Publication No. H09-103479

SUMMARY OF THE INVENTION

Problem to be Solved by the Invention

An object of the present invention is to provide an antiadhesive material which exerts an excellent antiadhesive effect.

Means for Solving the Problem

The present inventors have made extensive investigations to solve the above-described problem, and have found that an antiadhesive material including both (A) a peptide having an amino acid sequence of (A-1)-(X-Pro-Y)$_n$-[X represents any amino acid, Pro represents proline, Y represents hydroxyproline or proline, and n is an integer of 1 to 10], and/or a peptide having an amino acid sequence of (A-2)-(Pro-Y)$_m$-[Pro represents proline, Y represents hydroxyproline or proline, and m is an integer of 1 to 10], and (B) a gelatin gel has an extremely improved antiadhesive effect as compared to the case in which each of the components is used alone, and that the antiadhesive material exerts a remarkably excellent antiadhesive effect on, in particular, tendon adhesion. Further investigations have been made based on the above-described findings, and the present invention has been accomplished by the investigations.

Specifically, the present invention includes the following aspects.

Item 1. An antiadhesive material comprising:

(A) a peptide having an amino acid sequence of (A-1)-(X-Pro-Y)$_n$-[X represents any amino acid, Pro represents proline, Y represents hydroxyproline or proline, and n is an integer of 1 to 10] and/or a peptide having an amino acid sequence of (A-2)-(Pro-Y)$_m$-[Pro represents proline, Y represents hydroxyproline or proline, and m is an integer of 1 to 10]; and (B) a gelatin gel.

Item 2. The antiadhesive material according to item 1, wherein, in the amino acid sequence (A-1), X is a hydrophobic amino acid, a hydrophilic basic amino acid, or a hydrophilic neutral amino acid.

Item 3. The antiadhesive material according to item 1 or 2, wherein, in the amino acid sequence (A-1), X is glycine, isoleucine, asparagine, arginine, tyrosine, alanine, valine, or leucine.

Item 4. The antiadhesive material according to any one of items 1 to 3, wherein, in the amino acid sequence (A-1), Y is hydroxyproline.

Item 5. The antiadhesive material according to any one of items 1 to 4, wherein, in the amino acid sequence (A-1), X is glycine, isoleucine, asparagine, arginine, or tyrosine, and Y is hydroxyproline.

Item 6. The antiadhesive material according to any one of items 1 to 5, wherein, in the amino acid sequence (A-1), n is an integer of 1 to 5.

Item 7. The antiadhesive material according to item 1, wherein, in the amino acid sequence (A-2), m is an integer of 1 to 5.

Item 8. The antiadhesive material according to any one of items 1 to 7, wherein the gelatin gel is a crosslinked gelatin gel.

Item 9. The antiadhesive material according to any one of items 1 to 8, wherein the gelatin gel is a gelatin sponge gel.

Item 10. The antiadhesive material according to any one of items 1 to 9, wherein the gelatin gel is a powder-form aerogel or a granule-form hydrogel.

Item 11. The antiadhesive material according to any one of items 1 to 10, wherein the antiadhesive material further comprises an aqueous solvent, and is in hydrogel form containing the peptide and the gelatin gel.

Item 12. The antiadhesive material according to any one of items 1 to 10, wherein the antiadhesive material comprises no aqueous solvent, and is a one-part type which includes a solid formulation containing the peptide and the gelatin gel.

Item 13. The antiadhesive material according to any one of items 1 to 10, wherein the antiadhesive material is a two-part type which includes formulation I containing the peptide and formulation II containing the gelatin gel.

Item 14. The antiadhesive material according to item 13, wherein the formulation I is in liquid form containing an aqueous solvent, and the formulation II is in hydrogel form containing an aqueous solvent.

Item 15. The antiadhesive material according to item 13, wherein the formulation I is in liquid form containing an aqueous solvent, and the formulation II is in aerogel form.

Item 16. The antiadhesive material according to item 13, wherein the formulation I is in powder form, and the formulation II is in hydrogel form containing an aqueous solvent.

Item 17. The antiadhesive material according to item 13, wherein the formulation I is in powder form, and the formulation II is in aerogel form.

Item 18. A use of a formulation containing: (A) a peptide having an amino acid sequence of (A-1)-(X-Pro-Y)$_n$-[X represents any amino acid, Pro represents proline, Y represents hydroxyproline or proline, and n is an integer of 1 to 10], and/or a peptide having an amino acid sequence of (A-2)-(Pro-Y)$_m$-[Pro represents proline, Y represents hydroxyproline or proline, and m is an integer of 1 to 10]; and (B) a gelatin gel, for the manufacture of an antiadhesive material.

Item 19. A method for preventing adhesion, the method comprising administering the antiadhesive material according to any one of items 1 to 17 in an amount effective for preventing adhesion to a site of a biological tissue in need of preventing adhesion.

Advantages of the Invention

According to the antiadhesive material of the present invention, a remarkably excellent antiadhesive effect can be exerted by an interaction between a peptide containing a particular amino acid sequence and a gelatin gel. In addition, according to one aspect of the antiadhesive material according to the present invention, since both high levels of diffusibility into a target site and a physical barrier function can be achieved, an excellent antiadhesive effect can be exerted on a tendon which is surrounded by minute and intricate tissues.

EMBODIMENTS OF THE INVENTION

Figure 1:
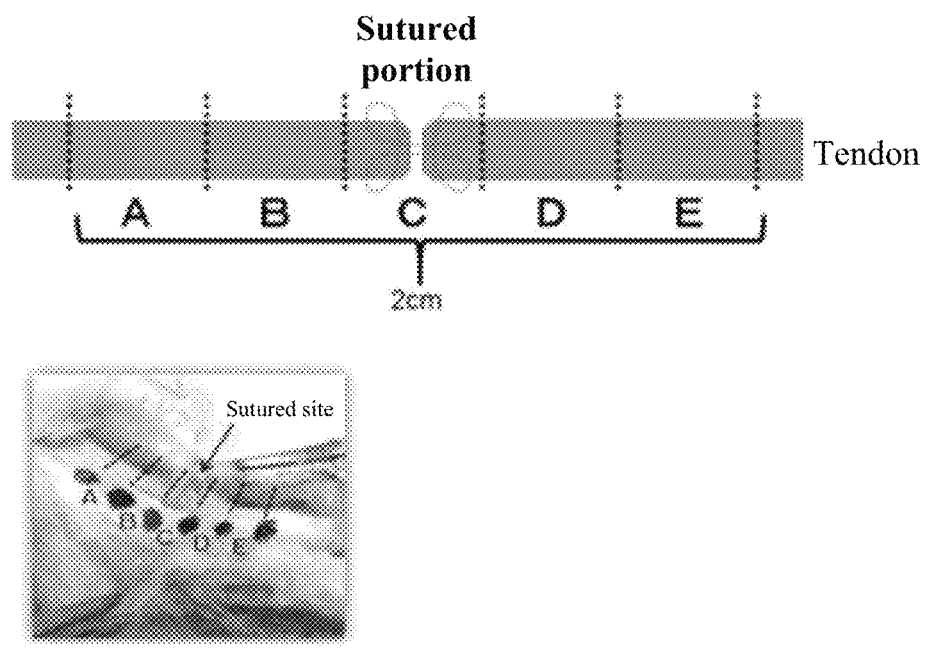
FIG. 1 shows an Achilles portion which was evaluated for degrees of adhesion in Test Examples 1 and 2.

The antiadhesive material of the present invention is characterized by comprising a peptide having a particular amino acid sequence and a gelatin gel. The antiadhesive material of the present invention will be described in detail below.

[Definition]

Herein, amino acids are denoted by the following three-letter abbreviations.

Ala: alanine
Arg: arginine
Asn: asparagine
Asp: aspartic acid
Cys: cysteine
Gln: glutamine
Glu: glutamic acid
Gly: glycine
His: histidine
Hyp: hydroxyproline
Ile: isoleucine
Leu: leucine
Lys: lysine
Met: methionine
Phe: phenylalanine
Pro: proline
Ser: serine
Thr: threonine
Trp: tryptophan
Tyr: tyrosine
Val: valine Herein, in expressions of a dipeptide and a tripeptide, the left end corresponds to the N terminus and the right end corresponds to the C terminus. For example, the expression "X-Pro-Y" of a tripeptide indicates that the left amino acid residue (X) is present at the N terminus and the right amino acid residue (Y) is present at the C terminus.

[Peptide]

The antiadhesive material of the present invention contains a peptide having the following amino acid sequence (A-1) and/or a peptide having the following amino acid sequence (A-2).

(A-1)-(X-Pro-Y)$_n$-[X represents any amino acid, Pro represents proline, Y represents hydroxyproline or proline, and n is an integer of 1 to 10.]

(A-2)-(Pro-Y)$_m$-[Pro represents proline, Y represents hydroxyproline or proline, and m is an integer of 1 to 10.]

In the amino acid sequence (A-1), X is any amino acid. Examples of X in the amino acid sequence (A-1) include a hydrophobic amino acid, a hydrophilic basic amino acid, a hydrophilic neutral amino acid, and the like. Specific examples of the hydrophobic amino acid include Gly, Ala, Val, Leu, Tyr, Ile, Met, Pro, Phe, Trp, and Cys. Specific examples of the hydrophilic basic amino acid include Arg, Lys, and His. Specific examples of the hydrophilic neutral amino acid include Asn, Gln, Ser, and Thr. Among amino acids included in X, from the standpoint of further improving the antiadhesive effect, examples include preferably Gly, Ile, Asn, Arg, Tyr, Ala, Val, Leu, Met, Pro, and Phe; more preferably Gly, Ile, Asn, Arg, Tyr, Ala, Val, Leu, and Phe; still more preferably Gly, Ile, Asn, Arg, Tyr, Ala, Val, and Leu; particularly preferably Gly, Ile, Asn, Arg, and Tyr; and most preferably Gly, Ile, Asn, and Arg.

In the amino acid sequence (A-1), Y is Hyp or Pro. From the standpoint of further improving the antiadhesive effect, examples of the amino acid included in Y include preferably Hyp.

In the amino acid sequence (A-1), specific examples of the tripeptide unit "X-Pro-Y" include, Gly-Pro-Hyp, Ile-Pro-Hyp, Asn-Pro-Hyp, Arg-Pro-Hyp, Tyr-Pro-Hyp, Ala-Pro-Hyp, Leu-Pro-Hyp, Val-Pro-Hyp, Phe-Pro-Hyp, Gly-Pro-Pro, Ile-Pro-Pro, Asn-Pro-Pro, Arg-Pro-Pro, Tyr-Pro-Pro, Ala-Pro-Pro, Leu-Pro-Pro, Val-Pro-Pro, Phe-Pro-Pro, and the like. Among these, from the standpoint of further improving the antiadhesive effect, examples include preferably Gly-Pro-Hyp, Ile-Pro-Hyp, Asn-Pro-Hyp, Arg-Pro-Hyp, Tyr-Pro-Hyp, Gly-Pro-Pro, Ile-Pro-Pro, Asn-Pro-Pro, Arg-Pro-Pro, and Tyr-Pro-Pro; more preferably Gly-Pro-Hyp, Ile-Pro-Hyp, Asn-Pro-Hyp, Arg-Pro-Hyp, and Tyr-Pro-Hyp; particularly preferably Gly-Pro-Hyp, Ile-Pro-Hyp, Asn-Pro-Hyp, Arg-Pro-Hyp.

In the amino acid sequence (A-1), n is the number of the tripeptide unit "X-Pro-Y", and is an integer of 1 to 10. That is, when n is 2, the amino acid sequence (A-1) has an amino acid sequence of "X-Pro-Y-X-Pro-Y". From the standpoint of further improving the antiadhesive effect, n is preferably 1 to 7, more preferably 1 to 5, still more preferably 1 to 3 or 1 or 2, and particularly preferably 1.

In the peptide having the amino acid sequence (A-1), one or more amino acids may be added to the N terminus and/or the C terminus of the amino acid sequence represented by -(X-Pro-Y)$_n$- as long as the peptide exerts a desired antiadhesive effect. Examples of the number of amino acids which can be added to the N terminus include 1 to 40, and preferably 1 to 20. Examples of the number of amino acids which can be added to the C terminus include 1 to 40, and preferably 1 to 20.

In the amino acid sequence (A-2), Y is Hyp or Pro. From the standpoint of further improving the antiadhesive effect, examples of the amino acid included in Y include preferably Hyp.

In the amino acid sequence (A-2), m is the number of dipeptide unit "Pro-Y", and is an integer of 1 to 10. That is, when m is 2, the amino acid sequence (A-2) has an amino acid sequence of "Pro-Y-Pro-Y". From the standpoint of further improving the antiadhesive effect, examples of m include preferably 1 to 7, more preferably 1 to 5, still more preferably 1 to 3 or 1 or 2, and particularly preferably 1.

In the peptide having the amino acid sequence (A-2), one or more amino acids may be added to the N terminus and/or the C terminus of the amino acid sequence represented by -(Pro-Y)$_m$- as long as the peptide exerts a desired antiadhesive effect. Examples of the number of amino acids which can be added to the N terminus include 1 to 40, and preferably 1 to 20. Examples of the number of amino acids which can be added to the C terminus include 1 to 40, and preferably 1 to 20.

In the antiadhesive material of the present invention, among peptides having the amino acid sequence (A-1) and peptides having the amino acid sequence (A-2), one peptide may be used alone, or two or more peptides may be used in combination.

The antiadhesive material of the present invention may contain peptides having other amino acid sequences together with the peptide having the above-described amino acid sequence. For example, an amino acid sequence of collagen contains a tripeptide unit "Gly-Pro-Hyp" and a dipeptide unit "Pro-Hyp", a tripeptide mixture obtained by hydrolysis of collagen contains Gly-Pro-Hyp, a dipeptide mixture obtained by hydrolysis of collagen contains Pro-Hyp. Such tripeptide mixture or dipeptide mixture can be used in the antiadhesive material of the present invention.

The tripeptide and the dipeptide used in the present invention can be obtained by hydrolysis of a naturally occurring polypeptide or a polypeptide obtained by bioengineering techniques, or can be obtained by chemical synthesis. For example, a tripeptide "Gly-Pro-Hyp" and a dipeptide "Pro-Hyp" can be obtained by a chemical synthesis method, or by hydrolysis of collagen or the like. Specifically, since collagen of mammals such as cattle, pigs, or the like, or fishes such as sharks, tilapia, salmons, Pangasius, or the like contains an amino acid sequence of the tripeptide unit "Gly-Pro-Hyp" and an amino acid sequence of the dipeptide unit "Pro-Hyp", the above-described tripeptide and dipeptide can be obtained from the above-described collagens.

[Gelatin Gel]

The antiadhesive material according to the present invention contains a gelatin gel.

Gelatin is a water-soluble protein obtained by denaturation of collagen of mammals such as cattle, pigs, or the like or fishes such as sharks, tilapia, salmons, Pangasius, or the like by heat, an acid, an alkaline, an enzyme, or the like. Gelatin is gradually hydrolyzed in vivo and excreted from the body, and thus is a highly biocompatible material.

The gelatin gel used in the present invention may be any of an uncrosslinked gelatin gel or a crosslinked gelatin gel. From the standpoint of further improving the antiadhesive effect, examples of the gelatin gel preferably include a crosslinked gelatin gel. When a crosslinked gelatin gel is used, since decomposition of gelatin in vivo can be retarded, the antiadhesive material of the present invention can be retained in the site of administration for a period required for preventing adhesion.

The crosslinked gelatin gel is a gel of crosslinked gelatin. Examples of the method for crosslinking gelatin include, but is not limited to, the following methods: heat crosslinking in which crosslinking is performed by application of heat; electron beam crosslinking in which crosslinking is performed by irradiation of electron beam such as ultraviolet rays or far-infrared rays; chemical crosslinking in which crosslinking is performed by treatment with glutaraldehyde, tannin, alum, aluminum sulfate, a succinimide-modified poly-L-glutamic acid, or the like; and enzyme crosslinking in which crosslinking is performed by treatment with an enzyme such as glutaminase. Examples of the crosslinked gelatin used in the present invention include preferably a crosslinked gelatin gel obtained by heat crosslinking from the standpoint of biocompatibility, an antiadhesive effect, and the like.

In addition, the gelatin gel used in the present invention is preferably a porous material. When the gelatin gel used is a porous material, a further improved antiadhesive effect can be achieved. Preferred examples of the porous gelatin gel include a gelatin sponge (sponge-like gelatin gel). The porous gelatin gel can be obtained by a known production method. As the gelatin sponge, for example, Spongel, Gelfoam, and the like are commercially available. Such a commercially available product can be used in the present invention.

A gelatin gel containing hyaluronic acid, trehalose, pectin, cyclodextrin, chitosan, or the like can be used as the gelatin gel used in the present invention. Such a gelatin gel can be produced by a known method.

The gelatin gel used in the present invention may be in a form of either an aerogel or a hydrogel. Herein, an aerogel refers to a gel containing air as a dispersion medium (i.e., dry gel). The aerogel includes a dry gel obtained by using a supercritical drying method (aerogel in a narrow sense), a dry gel obtained by drying under atmospheric pressure (xerogel), and a dry gel obtained by freeze-drying (cryogel). Herein, a hydrogel refers to a gel containing an aqueous solvent as a dispersion medium (i.e., wet gel). In the antiadhesive material of the present invention, which of the aerogel or the hydrogel should be used as a gelatin gel is suitably determined depending on dosage forms as described below.

Forms of the gelatin gel used in the present invention are not particularly limited as long as the gelatin gel is shaped so as to fit the shape of an application target site. The aerogel is preferably in powder form, and the hydrogel is preferably in granule form (this form is produced when a hydrogel in powder form has absorbed water). As described above, when a powder-form aerogel or a granule-form hydrogel is used, the antiadhesive material of the present invention becomes gel form having fluidity at an affected site, and thus the antiadhesive material becomes highly diffusible at an application target site after administration. Accordingly, even when the antiadhesive material is administered to a tendon, the antiadhesive material can favorably diffuse into minute and intricate tissues and spread over the affected site. In addition, the antiadhesive material can stay on the application target site for a certain period of time and can exert a physical barrier function. In particular, an aerogel in which a gelatin sponge is in powder form and a hydrogel in which the aerogel has absorbed water can exert a remarkably excellent antiadhesive effect, and thus are preferably used. The gelatin gel may be shaped into a sheet-like shape or a film-like shape, if necessary.

In the antiadhesive material of the present invention, when a powder-form aerogel is used as the gelatin gel, the particle size of the powder-form aerogel is not particularly limited. For example, the particle size of the powder-form aerogel (in a state in which no water has been absorbed) may be in the range of 200 to 750 μm, preferably in the range of 250 to 750 μm, and still more preferably in the range of 250 to 500 μm. The above-described particle size can be achieved by classifying particles according to a desired particle size using a sieve.

[Ratio Between Peptide and Gelatin Gel]

In the antiadhesive material of the present invention, the ratio between the peptide and the gelatin gel is not particularly limited as long as a desired antiadhesive effect can be exerted. For example, per 100 parts by weight of the gelatin gel as dry weight (i.e., as the weight of gelatin alone), the peptide may be 2 to 500 parts by weight, preferably 50 to 400 parts by weight, and more preferably 100 to 300 parts by weight.

[Antiadhesive Hydrogel]

The antiadhesive effect of the antiadhesive material of the present invention can be exerted by applying a hydrogel (hereinafter referred to as an "antiadhesive hydrogel") containing the above-described peptide, the above-described gelatin gel, and an aqueous solvent to a target site where prevention of adhesion is required.

Examples of the aqueous solvent used in the antiadhesive hydrogel include water, physiological saline, and the like.

In the antiadhesive hydrogel, it is sufficient that the peptide and the gelatin gel satisfy the above-described ratio, and the antiadhesive hydrogel contains an aqueous solvent in an amount suitable for achieving hydrogel form. Examples of the content of each component contained in the antiadhesive hydrogel are provided below.

Content of the peptide: for example, 1 to 50% by weight, preferably 3 to 40% by weight, and more preferably 10 to 30% by weight.

Content of the gelatin gel: for example, as dry weight (as the weight of gelatin alone), 5 to 50% by weight, preferably 10 to 40% by weight, and more preferably 15 to 30% by weight.

Content of the aqueous solvent: for example, 10 to 90% by weight, preferably 30 to 80% by weight, and more preferably 40 to 55% by weight.

In the antiadhesive material of the present invention, when a peptide mixture containing the peptide having the above-described amino acid sequence and a different peptide having a different amino acid sequence is used, it is preferred that the content of the peptide having the above-described amino acid sequence is as described above.

[Dosage Form and Method for Use]

The antiadhesive material of the present invention may be an antiadhesive material containing the above-described antiadhesive hydrogel itself.

Alternatively, the antiadhesive material may be an antiadhesive material which allows the above-described antiadhesive hydrogel to be prepared before use, or to be formed at an application target site. Hereinafter, the formulation which allows the above-described antiadhesive hydrogel to be prepared before use or to be formed at an application target site is denoted as an "antiadhesive material for preparing at the time of use".

Specific examples of the antiadhesive material for preparing at the time of use include a formulation which contains the above-described peptide and the above-described gelatin gel in the same composition (hereinafter, referred to as a "one-part type") and a formulation which contains the above-described peptide and the above-described gelatin gel in different compositions (hereinafter, referred to as a "two-part type"). The one-part type antiadhesive material for preparing at the time of use and the two-part type antiadhesive material for preparing at the time of use will be separately described below.

One-Part Type Antiadhesive Material for Preparing at the Time of Use

The one-part type antiadhesive material for preparing at the time of use is a solid form formulation in which the above-described tripeptide and the above-described aerogel-form gelatin gel are contained in the absence of water, and used by adding an aqueous solvent at the time of use.

In the one-part type antiadhesive material for preparing at the time of use, for example, when the gelatin gel is a powder-form aerogel, it is sufficient that the aerogel and the peptide are nixed, or the peptide is carried on the aerogel. When the gelatin gel is an aerogel shaped in a sheet-like shape or a film-like shape, it is sufficient that the peptide is carried on the aerogel.

In the one-part type antiadhesive material for preparing at the time of use, it is sufficient that the peptide and the gelatin gel are contained so as to satisfy the above-described ratio. Examples of the content of each component in the one-part type antiadhesive material for preparing at the time of use are provided below.

Content of the peptide: for example, 10 to 90% by weight, preferably 40 to 80% by weight, and more preferably 50 to 70% by weight.

Content of the gelatin gel: for example, as dry weight (as the weight of gelatin alone), 10 to 90% by weight, preferably 20 to 60% by weight, and more preferably 30 to 50% by weight.

Examples of the method of using the antiadhesive material of the above-described aspect include the following methods: a method including adding an aqueous solvent to the antiadhesive material before administration to prepare the above-described antiadhesive hydrogel, and administering the antiadhesive hydrogel to an application target site; or a method including administering the antiadhesive material as it is to an application target site, and thereafter adding an aqueous solvent to form the above-described antiadhesive hydrogel on an application target site.

In the antiadhesive material of the above-described aspect, the amount of the aqueous solvent used at the time of administration may be suitably determined such that the above-described antiadhesive hydrogel can eventually be formed. Specific examples of the amount of the aqueous solvent used include, per 100 parts by weight of the aerogel-form gelatin gel, 10 to 90 parts by weight, preferably 30 to 80 parts by weight, and more preferably 40 to 55 parts by weight.

Two-Part Type Antiadhesive Material for Preparing at the Time of Use

In the two-part type antiadhesive material for preparing at the time of use, formulation I containing the above-described tripeptide and formulation II containing the above-described gelatin gel are contained separately. The antiadhesive material of this aspect is used by mixing the formulation I and the formulation II, and an aqueous solvent if necessary, at the time of use, or impregnating the formulation I and the formulation II with an aqueous solvent at the time of use.

The formulation I may be in liquid form containing an aqueous solvent, or in powder form containing no aqueous solvent. The formulation II may be in hydrogel form containing an aqueous solvent, or in aerogel form containing no aqueous solvent. That is, aspects of the combinations of the formulation I and the formulation II in the two-part type antiadhesive material for preparing at the time of use include: (1) a combination of liquid-form formulation I and hydrogel-form formulation II, (2) a combination of liquid-form formulation I and aerogel-form formulation II, (3) a combination of powder-form formulation I and hydrogel-form formulation II, and (4) a combination of powder-form formulation I and aerogel-form formulation II. These aspects of the combinations will be separately described below.

(Combination of Liquid-form Formulation I and Hydrogel-form Formulation II)

The liquid-form formulation I contains the above-described tripeptide and an aqueous solvent.

The hydrogel-form formulation II contains the gelatin gel and an aqueous solvent. When a granule-form hydrogel, in which a powder-form aerogel has absorbed water, is used as the gelatin gel, the formulation II becomes gel form having fluidity. When a sheet-like or film-like shaped gelatin gel is used as the gelatin gel, the formulation II becomes a sheet-like or film-like form.

Contents of the above-described peptide and an aqueous solvent contained in the liquid-form formulation I, and contents of the gelatin gel and an aqueous solvent contained in the hydrogel-form formulation II may be suitably determined such that the antiadhesive hydrogel has the above-described composition when the formulation I and the formulation II are mixed at the time of use. Specific examples include a content within the following ranges.

Content of the above-described peptide contained in the formulation I: for example, 1 to 80% by weight, and preferably 3 to 50% by weight.

Content of an aqueous solvent contained in the formulation I: for example, 20 to 99% by weight, and preferably 50 to 97.

Content of the gelatin gel contained in the formulation II: for example, as dry weight (as the weight of gelatin alone), 1 to 80% by weight, and preferably 10 to 50% by weight.

Content of an aqueous solvent contained in the formulation II: for example, 20 to 99% by weight, and preferably 50 to 90% by weight.

The ratio between the formulation I and the formulation II to be administered may be suitably adjusted such that the antiadhesive hydrogel has the above-described composition after mixing of the formulation I and the formulation II. For example, the formulation II may be, per 100 parts by weight of the formulation I, 75 to 125 parts by weight, preferably 90 to 120 parts by weight, and more preferably 95 to 105 parts by weight.

Examples of the method of using the antiadhesive material of the above-described aspect include the following methods: a method including mixing the formulation I and the formulation II, and further adding an aqueous solvent if needed, to prepare the above-described antiadhesive hydrogel before administration, and thereafter administering the resulting antiadhesive hydrogel to an application target site; a method including administering the formulation Ito an application target site, thereafter administering the formulation II, and further adding an aqueous solvent if needed, to form the above-described antiadhesive hydrogel on the application target site; or a method including administering the formulation II to an application target site, thereafter administering the formulation I, and further adding an aqueous solvent if needed, to form the above-described antiadhesive hydrogel on the application target site. From the standpoint of convenience in administration, the method including mixing the formulation I and the formulation II, and further adding an aqueous solvent if needed, to prepare the above-described antiadhesive hydrogel before administration, and thereafter administering the resulting antiadhesive hydrogel to an application target site is preferred.

(Combination of Liquid-form Formulation I and Aerogel-form Formulation II)

The liquid-form formulation I contains the above-described peptide and an aqueous solvent.

The aerogel-form formulation II contains an aerogel-form gelatin gel. When a powder-form aerogel is used as the gelatin gel, the formulation II becomes powder form. When a sheet-like or film-like shaped gelatin gel is used as the gelatin gel, the formulation II becomes a sheet-like or film-like form.

Contents of the above-described peptide and an aqueous solvent contained in the liquid-form formulation I may be suitably determined such that the antiadhesive hydrogel has the above-described composition when the formulation I and the formulation II are mixed at the time of use. Specific examples include a content within the following range.

Content of the above-described peptide contained in the formulation I: for example, 1 to 80% by weight, and preferably 3 to 50% by weight.

Content of an aqueous solvent contained in the formulation I: for example, 20 to 99% by weight, and preferably 50 to 97.

The ratio between the formulation I and the formulation II to be administered may be suitably adjusted such that the antiadhesive hydrogel has the above-described composition after mixing of the formulation I and the formulation II. For example, the formulation II may be, per 100 parts by weight of the formulation I, 75 to 125 parts by weight, preferably 90 to 110 parts by weight, and more preferably 95 to 105 parts by weight.

Examples of the method of using the antiadhesive material of the above-described aspect include the following methods: a method including mixing the formulation I and the formulation II, and further adding an aqueous solvent if needed, to prepare the above-described antiadhesive hydrogel, and thereafter administering the resulting antiadhesive hydrogel to an application target site; a method including administering the formulation Ito an application target site, thereafter administering the formulation II, and further adding an aqueous solvent if needed, to form the above-described antiadhesive hydrogel on the application target site; or a method including administering the formulation II to an application target site, thereafter administering the formulation I, and further adding an aqueous solvent if needed, to form the above-described antiadhesive hydrogel on the application target site. From the standpoint of convenience in administration, the method including mixing the formulation I and the formulation II, and further adding an aqueous solvent if needed, to prepare the above-described antiadhesive hydrogel, and thereafter administering the resulting antiadhesive hydrogel to an application target site is preferred.

(Combination of Powder-form Formulation I and Hydrogel-form Formulation II)

The powder-form formulation I contains the above-described peptide.

The hydrogel-form formulation II contains the gelatin gel and an aqueous solvent. When a granule-form hydrogel, in which a powder-form aerogel has absorbed water, is used as the gelatin gel, the formulation II becomes gel form having fluidity. When a sheet-like or film-like shaped gelatin gel is used as the gelatin gel, the formulation II becomes a sheet-like or film-like form.

Contents of the gelatin gel and an aqueous solvent contained in the hydrogel-form formulation II may be suitably determined such that the antiadhesive hydrogel has the above-described composition when the formulation I and the formulation II are mixed at the time of use. Specific examples include a content within the following range.

Content of the gelatin gel contained in the formulation II: for example, 1 to 50% by weight, and preferably 10 to 30% by weight.

Content of the aqueous solvent contained in the formulation II: for example, 50 to 99% by weight, and preferably 70 to 90.

The ratio between the formulation I and the formulation II to be administered may be suitably adjusted such that the antiadhesive hydrogel has the above-described composition after mixing of the formulation I and the formulation II. For example, the formulation I may be, per 100 parts by weight of the formulation 11, 75 to 125 parts by weight, preferably 90 to 110 parts by weight, and more preferably 95 to 105 parts by weight.

Examples of the method of using the antiadhesive material of the above-described aspect include the following methods: a method including mixing the formulation I and the formulation II, and further adding an aqueous solvent if needed, to prepare the above-described antiadhesive hydrogel before administration, and thereafter administering the resulting antiadhesive hydrogel to an application target site; a method including administering the formulation I to an application target site, thereafter administering the formulation II, and further adding an aqueous solvent if needed, to form the above-described antiadhesive hydrogel on the application target site; or a method including administering the formulation II to an application target site, thereafter administering the formulation I, and further adding an aqueous solvent if needed, to form the above-described antiadhesive hydrogel on the application target site. From the standpoint of convenience in administration, the method including mixing the formulation I and the formulation II, and further adding an aqueous solvent if needed, to prepare the above-described antiadhesive hydrogel before administration, and thereafter administering the resulting antiadhesive hydrogel to an application target site is preferred.

(Combination of Powder-form Formulation I and Aerogel-form Formulation II)

The powder-form formulation I contains the above-described peptide.

The aerogel-form formulation II contains an aerogel-form gelatin gel. When a powder-form aerogel is used as the gelatin gel, the formulation II becomes powder form. When a sheet-like or film-like shaped gelatin gel is used as the gelatin gel, the formulation II becomes a sheet-like or film-like form.

The ratio between the formulation I and the formulation II to be administered may be adjusted such that the antiadhesive hydrogel has the above-described composition after mixing of the formulation I, the formulation II, and an aqueous solvent which are to be administered. For example, the formulation II may be, per 100 parts by weight of the formulation I, 75 to 125 parts by weight, preferably 90 to 110 parts by weight, and more preferably 95 to 125 parts by weight.

Examples of the method of using the antiadhesive material of the above-described aspect include the following methods: a method including mixing the formulation I, the formulation II, and an aqueous solvent to prepare the above-described antiadhesive hydrogel before administration, and thereafter administering the resulting antiadhesive hydrogel to an application target site; a method including mixing the formulation I and the formulation II before administration, administering the resulting mixture to an application target site, and further adding an aqueous solvent to the mixture to form the above-described antiadhesive hydrogel on the application target site; a method including administering the formulation II to an application target site, and thereafter administering the formulation I to which an aqueous solvent has been added to from the above-described antiadhesive hydrogel on the application target site; or a method including administering the formulation I to an application target site, thereafter adding an aqueous solvent to the formulation II to form a hydrogel, administering the resulting hydrogel to an application target site to form the above-described antiadhesive hydrogel on the application target site. From the standpoint of convenience in administration, the method including mixing the formulation I, the formulation II, and an aqueous solvent to prepare the above-described antiadhesive hydrogel before administration, and thereafter administering the resulting antiadhesive hydrogel to an application target site is preferred.

The antiadhesive material of the above-described aspect may be used without using an aqueous solvent. Specifically, examples of such a method of using the antiadhesive material include the following methods: a method including mixing the formulation I and the formulation II before administration, and thereafter administering the mixture to an application target site; a method including administering the formulation I to an application target site, and thereafter administering the formulation II; or a method including administering the formulation II to an application target site, and thereafter administering the formulation I. From the standpoint of convenience in administration, the method including mixing the formulation I and the formulation II before administration, and thereafter administering the mixture to an application target site is preferred. In such a method of using the antiadhesive material, blood or the like present in the application target site is used as an aqueous solvent for forming the antiadhesive hydrogel.

In the antiadhesive material of the above-described aspect, when an aqueous solvent is used at the time of administration, the amount of the aqueous solvent used may be suitably determined such that the antiadhesive hydrogel has the above-described composition when the formulation I, the formulation II, and the aqueous solvent are mixed at the time of use. Specifically, the aqueous solvent may be used, per 100 parts by weight in total of the formulation I and the formulation II, in an amount of 10 to 900 parts by weight, preferably 20 to 250 parts by weight, and more preferably 80 to 150 parts by weight.

[Other Ingredients]

The antiadhesive material of the present invention may contain pharmacological components such as antibacterial agents, antibiotics, anti-inflammatory agents, blood circulation improvers, steroids, enzyme inhibitors, a growth factor, and various vitamins, if needed, in addition to the above-described components for the purpose of enhancing therapeutic effects or preventing microbial infections. Since the antiadhesive material of the present invention stays in an application target site for a certain period of time, when the antiadhesive material contains the above-described pharmacological components, the antiadhesive material may be used as a sort of drug delivery system intended for sustained release of the pharmacological components.

The antiadhesive material of the present invention may further contain additives such as excipients, a binder, a lubricant, a pH adjustor, a buffer, an antiseptic, an antioxidant, a coloring agent, and a dehumidifying, if needed.

When the antiadhesive material of the present invention is a two-part type antiadhesive material for preparing at the time of use, these pharmacological components and additives may be contained in one of the formulation I and the formulation II, or may be contained in both of the formulation i and the formulation II.

[Use]

The antiadhesive material of the present invention may be used for preventing adhesion of biological tissues when a surgical operation such as incision or an endoscopic operation has been performed in a field of surgery for abdominal organs or the like and a field of orthopedic surgery for a tendon, a nerve, or a joint. In particular, among the sites in which prevention of adhesion is required, since a tendon is surrounded by minute and intricate tissues, the antiadhesive material is required to have excellent diffusibility to spread over the surrounding tissues of a tendon. When an aerogel-form gelatin gel powder or a granule-form hydrogel, in which the aerogel-form gelatin gel powder has absorbed water, is used, the antiadhesive material of the present invention can sufficiently satisfy properties required as an antiadhesive material for a tendon. In view of such an advantageous effects of the present invention, preferred examples of the target for preventing adhesion include a tendon.

When the antiadhesive material of the present invention is administered in hydrogel form, the antiadhesive material can favorably diffuse after administration. Thus, when the antiadhesive material is administered around a target site, the antiadhesive material can spread over the target site. Alternatively, when the antiadhesive material of the present invention is administered in powder form, the antiadhesive material may be administered to the target site entirely.

As a dose of the antiadhesive material of the present invention, an effective amount for preventing adhesion may be suitably determined according to conditions of an application target site. For example, the antiadhesive material may be administered in an amount corresponding to about 20 to 120 mg of a gelatin gel as dry weight (as the weight of gelatin alone) per square centimeter of an application target site where prevention of adhesion is required.

EXAMPLES

The present invention will be described below in detail based on examples and the like, but the present invention is not limited thereto.

1. Preparation and Provision of Test Material 1-1. Preparation of Gelatin Sponge Gel Powder A crosslinked-gelatin sponge gel powder which were used in the following test examples were prepared according to the following procedure.

1-1-1. Preparation of Crosslinked-Gelatin Sponge Gel Powder (A)

A crosslinked-gelatin sponge gel (trade name: "Spongel", Astellas Pharma Inc.) was crushed into powder having a particle diameter of 500 μm or less using an ultracentrifugal mill. Only powder having a particle diameter of 250 to 500 μm was recovered using a sieve to obtain crosslinked-gelatin sponge gel powder (A).

1-1-2. Preparation of Crosslinked-Gelatin Sponge Gel Powder (B)

In distilled water, 2.5% by weight of Gelatin (trade name: "RM-100", JELLICE Co., Ltd.) was dissolved to give a gelatin solution. The gelatin solution was subjected to preliminary freezing (−40° C., 12 hours), and thereafter freeze-dried (about −45° C., 40 hours) to give a gelatin sponge. The resulting gelatin sponge was subjected to heat crosslinking (140° C., 48 hours) using a convection oven, crushed into powder having a particle diameter of 500 μm or less using an ultracentrifugal mill. Only powder having a particle diameter of 250 to 500 μm was recovered using a sieve to obtain crosslinked-gelatin sponge gel powder (B).

1-1-3. Preparation of Crosslinked-Gelatin Sponge Gelpowder (C)

Crosslinked-gelatin sponge gel powder (C) was prepared and obtained as in the preparation of the crosslinked-gelatin sponge gel powder (B) except that the gelatin concentration in the gelatin solution was 10% by weight.

1-1-4. Preparation of Crosslinked-Gelatin Sponge Gel Powder (D)

Crosslinked-gelatin sponge gel powder (D) was prepared and obtained as in the preparation of the crosslinked-gelatin sponge gel powder (A) except that "BeMatriX Gelatin LS-H" (trade name of Nitta Gelatin Inc.) was used as the gelatin.

1-2. Provision of Peptide

The following various peptides were provided.

Tripeptide Mixture 1

A peptide mixture obtained by hydrolyzing collagen from pig skin (trade name: "Tp-100", JELLICE CO., LTD.).

The peptide mixture contains 90% by weight of tripeptides.

The peptide mixture contains, per 100 parts by weight in total of the tripeptides, 33.3 parts by weight of Gly-Pro-Hyp, 3.7 parts by weight of Gly-Ala-Hyp, 14.8 parts by weight of Gly-Pro-Ala, and 48.1 parts by weight of other tripeptides.

Tripeptide 2

A synthetic tripeptide of Gly-Ala-Hyp (Bachem AG, H-3260).

Tripeptide 3

A synthetic tripeptide of Gly-Pro-Ala (Bachem AG, H-3615).

Tripeptide 4

A synthetic tripeptide of Gly-Pro-Hyp (Bachem AG, H-3630).

Tripeptide 5

A synthetic tripeptide of Ile-Pro-Hyp (synthesized by PEPTIDE INSTITUTE, INC., which is an outsourced company).

Tripeptide 6

A synthetic tripeptide of Asn-Pro-Hyp (synthesized by PEPTIDE INSTITUTE, INC., which is an outsourced company).

Tripeptide 7

A synthetic tripeptide of Arg-Pro-Hyp (synthesized by PEPTIDE INSTITUTE, INC., which is an outsourced company).

Tripeptide 8

A synthetic tripeptide of Tyr-Pro-Hyp (PEPTIDE INSTITUTE, INC., which is an outsourced company).

Oligopeptide 1

A synthetic oligopeptide of $(Gly-Pro-Hyp)_5$ (15 amino acid residues) (PEPTIDE INSTITUTE, INC., 4032).

Polypeptide 1

A synthetic polypeptide of $(Gly-Pro-Hyp)_{10}$ (30 amino acid residues) (PEPTIDE INSTITUTE, INC., 4033)

Dipeptide 1

A synthetic dipeptide of Pro-Hyp (Bachem AG, G-3025).

Dipeptide 2

A synthetic dipeptide of Gly-Pro (PEPTIDE INSTITUTE, INC., 3052).

2. Test Example 1

2-1. Preparation of Test Sample

Test samples having compositions as shown in Table 1 were prepared.

TABLE 1

| Test sample | Composition |
| --- | --- |
| Comparative Example 1-1 | Physiological saline (Otsuka Pharmaceutical Factory, Inc.) |
| Comparative Example 1-2 | Physiological saline containing tripeptide mixture 1 (3% by weight) |
| Comparative Example 1-3 | Hydrogel composition containing mixture of crosslinked-gelatin sponge gel powder (A) (20% by weight) and physiological saline (80% by weight) |
| Example 1 | Hydrogel composition containing mixture of tripeptide mixture 1 (3% by weight), crosslinked-gelatin sponge gel powder (A) (20% by weight), and physiological saline (77% by weight) |

2-2. Evaluation of Antiadhesive Effect

As supplied animals, 13-week old rabbits (Kbl: JW, male) were used. Ketamine (trade name: "Ketalar for intramuscular injection 500 mg", DAIICHI SANKYO PROPHARMA CO., LTD.) and xylazine (trade name: "Selactar 2% injection") were mixed at a ratio of 20 parts by volume of xylazine per 100 parts by volume of ketamine, and the mixture was administered as anesthetics to a rabbit at a dose of 1.45 ml/kg body weight by intramuscular injection. Next, buprenorphine (trade name: "Lepetan injection 0.2 mg", Otsuka Pharmaceutical CO., LTD.) was administered as an analgesic drug at a dose of 20 μg/kg body weight by intramuscular injection, and enrofloxacin (Baytril 2.5% injection, Bayer Yakuhin, Ltd.) was administered as an antibacterial drug at a dose of 4 mg/kg body weight by subcutaneous injection.

Hair of the left hind limb of an animal was removed under anesthesia. Next, the rabbit was held by a holder (trade name: "a Kitajima-type rabbit holder", Natsume Seisakusho Co, Ltd.), and the area around the site to be operated was sterilized. The skin covering an Achilles tendon of the left hind limb was incised longitudinally to expose the Achilles tendon. The center of the exposed Achilles tendon was cut by sharp dissection using a scalpel. Then, the dissected region of the Achilles tendon was sutured with a suture (trade name: "5-0 Mersilene", Ethicon, Inc.) by a modified Kessler technique, and hemostasis and washing with physiological saline were performed. Then, 0.5 mL of a test sample was administered to the exposed Achilles tendon and its surroundings. Thereafter, the incised portion was sutured with a suture (trade name: "3-0 suture with needle for clinical use", Matsuda Ika Kogyo CO., LTD.), and the left hind limb of the rabbit was immobilized by gypsum (trade name: "Scotchcast™ Plus-J Casting Tape", 3M Japan Limited).

At 2 weeks after administration of the test sample, the operated site was incised again, and degrees of adhesion at 5 portions of the Achilles tendon (A to E shown in FIG. 1) were evaluated according to the criteria and represented by the scores shown below.

<Adhesion Score>
0: No adhesion
1: Easily dissectable from surrounding tissues by blunt dissection
2: Dissectable from surrounding tissues by blunt dissection
3: Dissection from surrounding tissues requires slightly sharp dissection
4: Dissection from surrounding tissues requires completely sharp dissection Each test was performed using 6 rabbits in each of Comparative Examples 1-1 and 1-2, and 5 rabbits in each of Comparative Example 1-3 and Example 1. The total score of the 5 portions in each rabbit was designated as an adhesion score of the individual rabbit, and the average of the adhesion scores in each group was calculated. In addition, at 2 weeks after administration of the test sample, whether the test sample remained on the Achilles tendon or not was visually evaluated.

Figure 2:
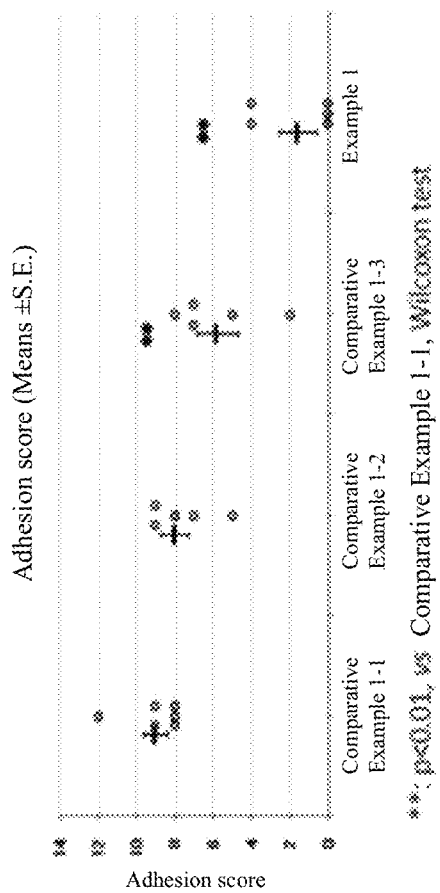
FIG. 2 shows the results of evaluation of antiadhesive effect in an Achilles tendon in Test Example 1.

The results obtained are shown in FIG. 2. From the results, when collagen-derived tripeptide mixture 1 containing Gly-Pro-Hyp (Comparative Example 1-2) or a hydrogel containing crosslinked-gelatin sponge gel (A) (Comparative Example 1-3) was administered alone, a limited antiadhesive effect was exerted. When both collagen-derived tripeptide mixture 1 containing Gly-Pro-Hyp and the hydrogel containing crosslinked-gelatin sponge gel (A) (Example 1) were administered, the antiadhesive effect was tremendously improved as compared to the case in which collagen-derived tripeptide mixture 1 containing Gly-Pro-Hyp or the hydrogel containing crosslinked-gelatin sponge gel (A) was administered alone.

3. Test Example 2

3-1. Preparation of Test Sample

Test samples having the compositions shown in Table 2 were prepared.

TABLE 2

| Test sample | Composition |
| --- | --- |
| Comparative Example 2 | Physiological saline (Otsuka Pharmaceutical Factory, Inc.) |

TABLE 2-continued

| Test sample | Composition |
| --- | --- |
| Example 2 | Formulation I including physiological saline containing tripeptide mixture 1 (30% by weight) and Formulation II including crosslinked-gelatin sponge gel powder (A) |

3-2. Evaluation of Antiadhesive Effect

Using 13-week old rabbits (Kbl: JW, male), by the same procedure as in the above-described Test Example 1, an Achilles tendon was cut and sutured, hemostasis and washing with physiological saline were performed, and thereafter a test sample was administered to the exposed Achilles tendon and its surroundings. Each test sample was administered as follows. In Comparative Example 2, 0.5 mL of the test sample was administered. In Example 2, 0.1 g of formulation II was administered, and thereafter 0.4 mL of formulation I was administered on the formulation II.

After administration of the test sample, incised portion was sutured, and the rabbit was immobilized by gypsum. At 4 weeks after administration of the test sample, degrees of adhesion of the Achilles tendon were evaluated by the same procedure as in the above-described Test Example 1. Each test was performed using 5 rabbits in Comparative Example 2, and 6 rabbits in Example 2.

Figure 3:
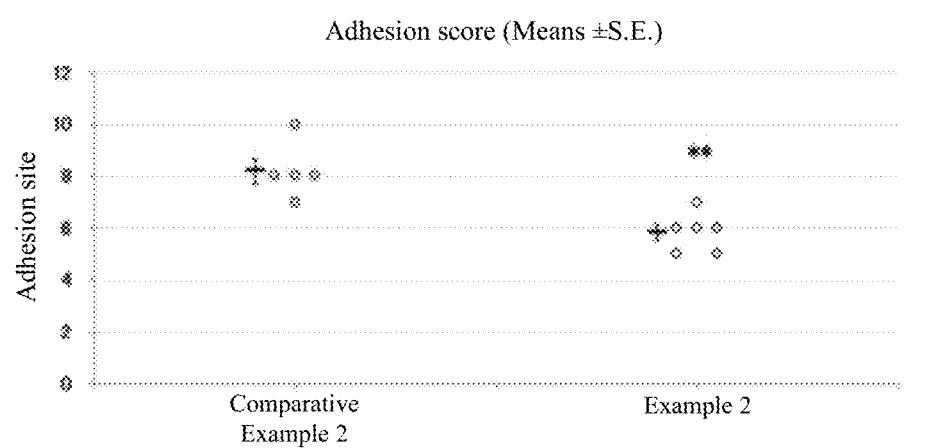
FIG. 3 shows the results of evaluation of antiadhesive effect in an Achilles tendon in Test Example 2.

The results obtained are shown in FIG. 3. From the results, it was found that when both collagen-derived tripeptide mixture 1 containing Gly-Pro-Hyp and crosslinked-gelatin sponge gel powder (A) were administered, even at 4 weeks after the operation, an antiadhesive effect was observed.

4. Test Example 3

4-1. Preparation of Test Sample

Test samples having compositions as shown in Table 3 were prepared.

TABLE 3

| Test sample | Composition |
| --- | --- |
| Comparative Example 3 | Physiological saline (Otsuka Pharmaceutical Factory, Inc.) |
| Example 3-1 | Formulation I including physiological saline containing tripeptide mixture 1 (3% by weight) and formulation II including crosslinked-gelatin sponge gel powder (A) |
| Example 3-2 | Hydrogel composition containing mixture of tripeptide mixture 1 (3% by weight), crosslinked-gelatin sponge gel powder (A) (20% by weight), and physiological saline (77% by weight) |

4-2. Evaluation of Antiadhesive Effect

As supplied animals, 13-week old rabbits (Kbl: JW, male) were used. By the same procedure as in the above-described Test Example 1, anesthesia, hair removal, holding, and sterilization were performed. Next, the skin covering a metatarsus of the left hind limb was incised longitudinally under anesthesia to expose flexor tendons. Among the exposed flexor tendons, a flexor digitorum profundus tendon was cut by sharp dissection using a scalpel. Then, the dissected region of the flexor digitorum profundus tendon was sutured with a suture (trade name: "6-0 Prolene", Ethicon, Inc.) by a modified Kessler technique, hemostasis and washing with physiological saline were performed. Then, test samples were administered to the exposed flexor digitorum profundus tendon and its surroundings. The test samples were administered as follows. In Comparative Example 3, 0.1 mL of the test sample was administered. In Example 3-1, 0.02 g of formulation II was administered, and thereafter 0.08 mL of formulation I was administered on the formulation II. In Example 3-2, 0.1 mL of the test sample was administered. Then, the incised portion was sutured with a suture (trade name: "5-0 suture with needle for clinical use", Matsuda Ika Kogyo CO., LTD.). The rabbit was fed with an e-collar around the neck to prevent self-injurious behavior.

At 2 weeks after administration of the test sample, the rabbit was painlessly sacrificed by an overdose of Somnopentil (a trade name "pentobarbital sodium", Kyoritsu Seiyaku Corporation) by auricular vein administration. The operated site was incised again, and degrees of adhesion were evaluated according to the criteria with respect to the following three portions: between flexor digitorum profundus tendon and gliding floor, between flexor digitorum profundus tendon and flexor digitorum superficialis tendon, and between flexor digitorum profundus tendon and other surrounding tissues. The total of the scores of the three portions was designated as a score for the individual.

<Evaluation Criteria>
0: No adhesion
1: Easily dissectable from surrounding tissues by blunt dissection
2: Dissectable from surrounding tissues by blunt dissection
3: Dissection from surrounding tissues requires slightly sharp dissection
4: Dissection from surrounding tissues requires completely sharp dissection The range of joint motion was measured as follows. At 2 weeks after administration of the test sample, the left hind limb of a rabbit was amputated between the talus and the tibia. The amputated left hind limb was placed on a measuring table. Next, a thread was attached to flexor digitorum profundus tendon of a proximal portion of MP joint, and the thread and a tensile tester was joined together through a hook. The tensile tester was configured with a force gauge (trade name: "Digital Force Gauge ZP-500N", IMADA CO., LTD.) and a test stand (trade name: "horizontal motorized test stand MH2-500N", IMADA CO., LTD.). Then, loads (0.5, 1.0, 2.0, and 3.0 N) were applied to the tendon. Photographic images were obtained before and after application of the load. The range of joint motion was calculated by the following formula.

Range of joint motion(°)=before application of load (flexion angle of PIP joint+flexion angle of DIP joint)−after application of load (flexion angle of PIP joint+flexion angle of DIP joint)   [Numerical Formula 1]

Figure 4:
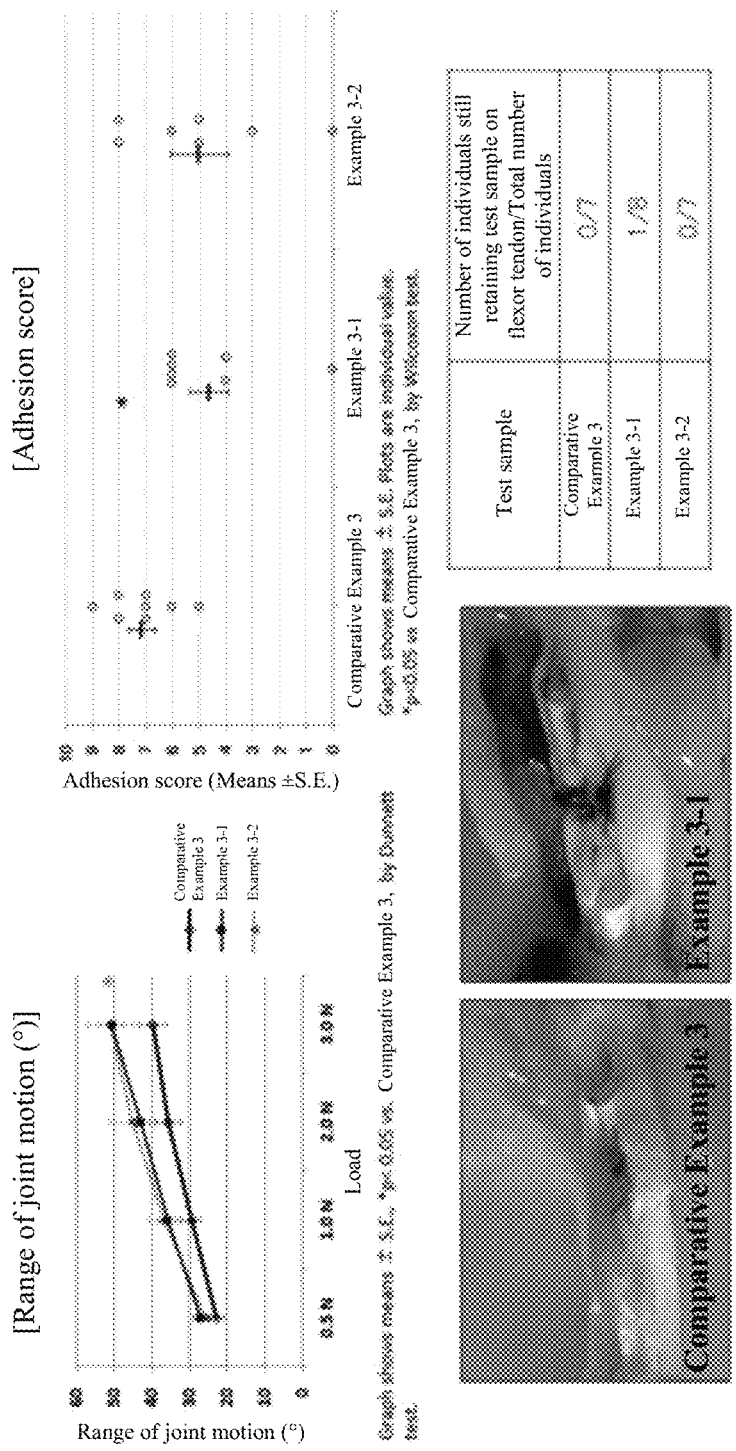
FIG. 4 shows the results of evaluation of antiadhesive effect in a flexor tendon in Test Example 3.

The results obtained are shown in FIG. 4. Photographic images of the state of the flexor tendon observed at the end of the test are also shown in FIG. 4. From the results, it was confirmed that when both collagen-derived tripeptide mixture 1 containing Gly-Pro-Hyp and the crosslinked-gelatin sponge gel were administered, adhesion can be prevented and the range of joint motion can be expanded.

5. Test Example 4

5.-1. Preparation of Test Sample

Test samples having compositions as shown in Table 4 were prepared.

TABLE 4

| Test sample | Composition |
| --- | --- |
| Comparative Example 4 | Physiological saline (Otsuka Pharmaceutical Factory, Inc.) |
| Example 4-1 | Hydrogel composition containing mixture of tripeptide mixture 1 (30% by weight), crosslinked-gelatin sponge gel powder (B) (20% by weight), and physiological saline (50% by weight) |
| Example 4-2 | Hydrogel composition containing mixture of tripeptide mixture 1 (30% by weight), crosslinked-gelatin sponge gel powder (C) (20% by weight), and physiological saline (50% by weight) |

5-2. Evaluation of Antiadhesive Effect

An antiadhesive effect was evaluated by the same procedure as in the above-described Test Example 3. The amount of each test sample administered was 0.2 mL. Each test was performed using 12 rabbits in Comparative Example 4, 8 rabbits in Example 4-1, and 9 rabbits in Example 4-2.

Figure 5:
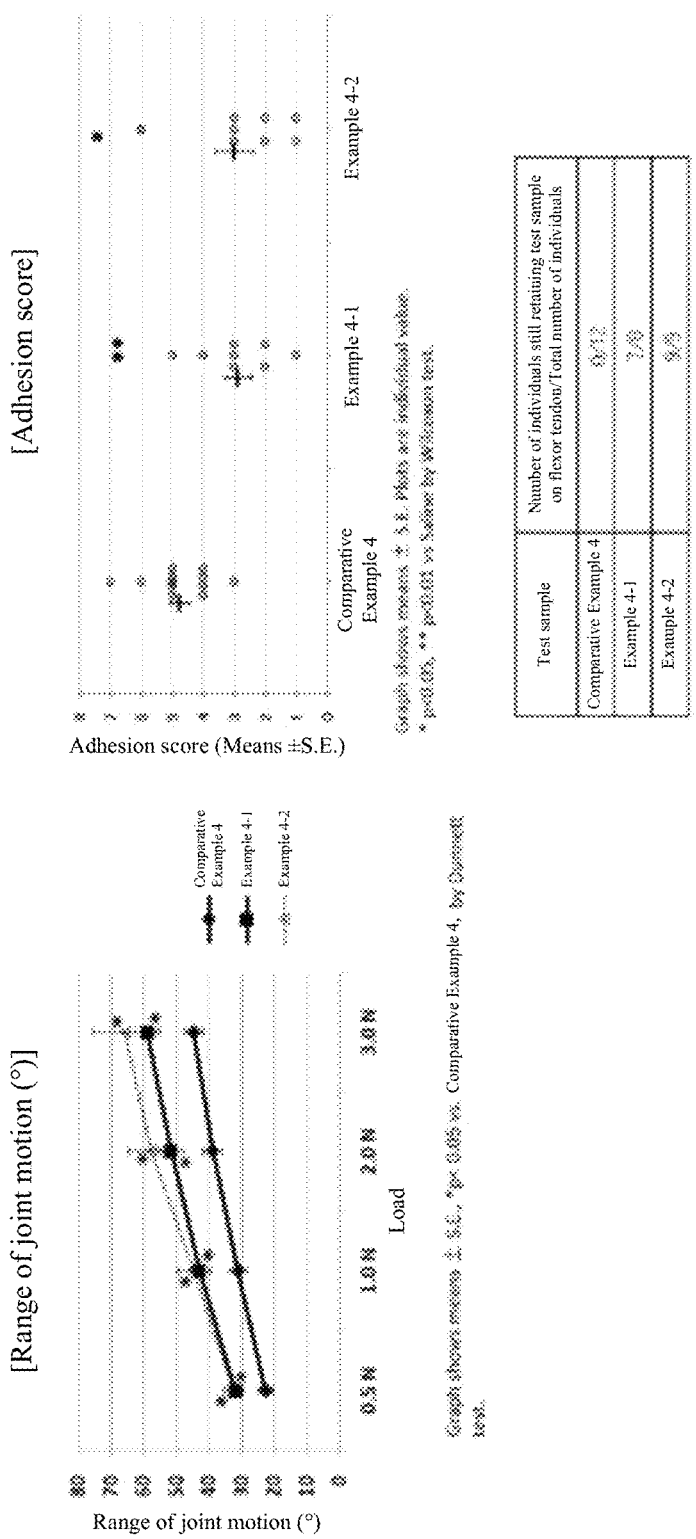
FIG. 5 shows the results of evaluation of antiadhesive effect in a flexor tendon in Test Example 4.

The results obtained are shown in FIG. 5. From the results, it was confirmed that when both tripeptide mixture 1 containing Gly-Pro-Hyp and the crosslinked-gelatin sponge gel were administered, adhesion can be prevented and the range of joint motion can be expanded. In addition, when crosslinked-gelatin sponge gel (B) or (C) was used (Example 4-1 and 4-2), as compared to the case in which crosslinked-gelatin sponge gel (A) was used (Examples 3-1 and 3-2 in the above-described Test Example 3), the ratio of individuals in which the test samples remained on the affected flexor tendon at 2 weeks after administration was high, and thus it was confirmed that the antiadhesive effect was improved.

6. Test Example 5

6-1. Preparation of Test Sample

Test samples having compositions as shown in Table 5 were prepared.

TABLE 5

| Test sample | Composition |
| --- | --- |
| Comparative Example 5-1 | Physiological saline (Otsuka Pharmaceutical Factory, Inc.) |
| Example 5-1 | Hydrogel composition containing mixture of tripeptide mixture 1 (30% by weight), crosslinked-gelatin sponge gel powder (B) (20% by weight), and physiological saline (50% by weight) |
| Comparative Example 5-2 | Hydrogel composition containing mixture of tripeptide 2 (30% by weight), crosslinked-gelatin sponge gel powder (B) (20% by weight), and physiological saline (50% by weight) |
| Comparative Example 5-3 | Hydrogel composition containing mixture of tripeptide 3 (30% by weight), crosslinked-gelatin sponge gel powder (B) (20% by weight), and physiological saline (50% by weight) |
| Example 5-2 | Hydrogel composition containing mixture of tripeptide 4 (30% by weight), crosslinked-gelatin sponge gel powder (B) (20% by weight), and physiological saline (50% by weight) |
| Comparative Example 5-4 | Hydrogel composition containing mixture of crosslinked-gelatin sponge gel powder (B) (20% by weight) and physiological saline (80% by weight) |

6-2. Evaluation of Antiadhesive Effect

An antiadhesive effect was evaluated by the same procedure as in the above-described Test Example 3. The amount of each test sample administered was 0.15 mL. Each test was performed using 6 rabbits in each of Comparative Example 5-1 and Examples 5-1 and 5-2, and 7 rabbits in each of Comparative Examples 5-2, 5-3, and 5-4.

Figure 6:
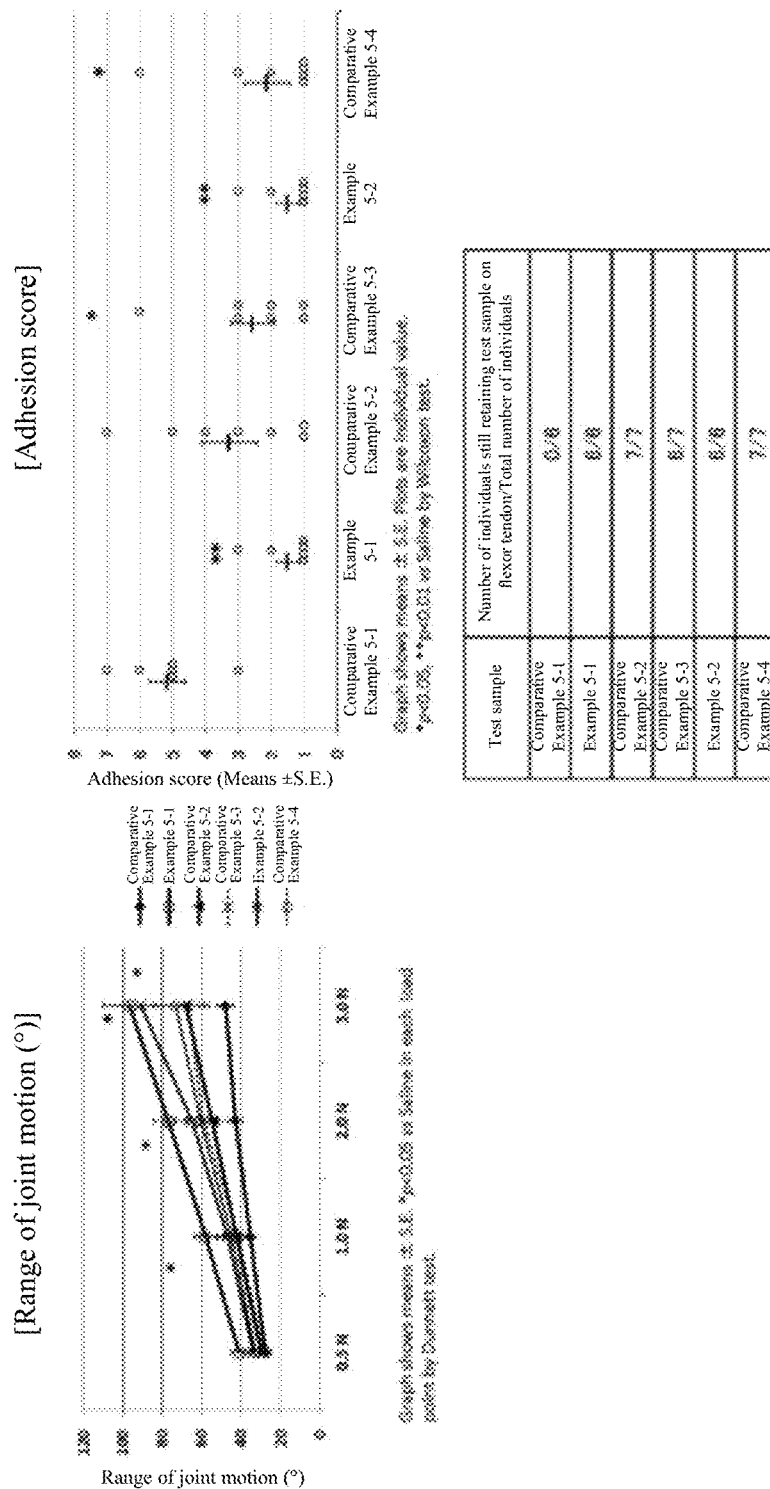
FIG. 6 shows the results of evaluation of antiadhesive effect in a flexor tendon in Test Example 5.

The results obtained are shown in FIG. 6. From the results, when both tripeptide 4 (Gly-Pro-Hyp) and the crosslinked-gelatin sponge gel were administered, the same antiadhesive effect as in the case in which both peptide mixture 1 and the crosslinked-gelatin sponge gel were administered was observed. On the other hand, in the cases in which tripeptide 2 (Gly-Ala-Hyp) and tripeptide 3 (Gly-Pro-Ala) were used, the antiadhesive effect was inferior to the case in which peptide mixture 1 was used.

7. Test Example 6
7-1. Preparation of Test Sample

Test samples having compositions as shown in Table 6 were prepared.

TABLE 6

| Test sample | Composition |
| --- | --- |
| Comparative Example 6-1 | Physiological saline (Otsuka Pharmaceutical Factory, Inc.) |
| Example 6-1 | Hydrogel composition containing mixture of tripeptide 4 (30% by weight), crosslinked-gelatin sponge gel powder (B) (20% by weight), and physiological saline (50% by weight) |
| Comparative Example 6-2 | Hydrogel composition containing mixture of dipeptide 2 (30% by weight), crosslinked-gelatin sponge gel powder (B) (20% by weight), and physiological saline (50% by weight) |
| Example 6-2 | Hydrogel composition containing mixture of dipeptide 1 (30% by weight), crosslinked-gelatin sponge gel powder (B) (20% by weight), and physiological saline (50% by weight) |

7-2. Evaluation of Antiadhesive Effect

An antiadhesive effect was evaluated by the same procedure as in the above-described Test Example 3. The amount of each test sample administered was 0.15 mL. Each test was performed using 9 rabbits in each of Comparative Example 6-1 and Examples 6-1 and 6-2, and 5 rabbits in Comparative Example 6-2.

Figure 7:
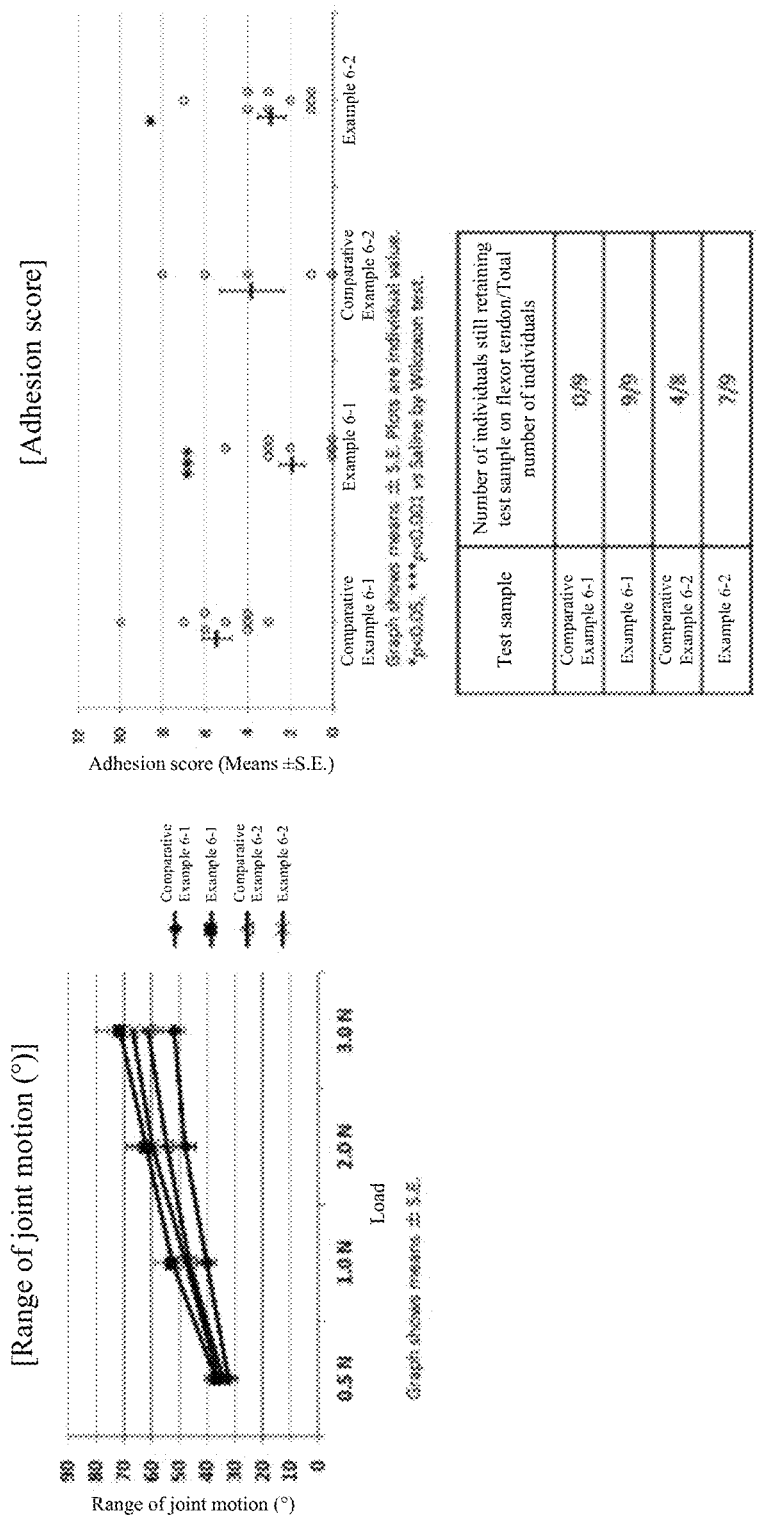
FIG. 7 shows the results of evaluation of antiadhesive effect in a flexor tendon in Test Example 6.

The results obtained are shown in FIG. 7. From the results, when dipeptide 2 (Gly-Pro) was used, as compared to the cases in which tripeptide 4 (Gly-Pro-Hyp) and dipeptide 1 (Pro-Hyp) were used, the antiadhesive effect was decreased. That is, it was found that the amino acid sequence of Gly-Pro-Hyp and the amino acid sequence of Pro-Hyp contribute to the antiadhesive effect.

8. Test Example 7
8-1. Preparation of Test Sample

Test samples having compositions as shown in Table 7 were prepared.

TABLE 7

| Test sample | Composition |
| --- | --- |
| Comparative Example 7 | Physiological saline (Otsuka Pharmaceutical Factory, Inc.) |
| Example 7-1 | Hydrogel composition containing mixture of tripeptide 4 (30% by weight), crosslinked-gelatin sponge gel powder (B) (20% by weight), and physiological saline (50% by weight) |

TABLE 7-continued

| Test sample | Composition |
| --- | --- |
| Example 7-2 | Hydrogel composition containing mixture of oligopeptide 1 (30% by weight), crosslinked-gelatin sponge gel powder (B) (20% by weight), and physiological saline (50% by weight) |
| Example 7-3 | Hydrogel composition containing mixture of polypeptide 1 (30% by weight), crosslinked-gelatin sponge gel powder (B) (20% by weight), and physiological saline (50% by weight) |

8-2. Evaluation of Antiadhesive Effect

An antiadhesive effect was evaluated by the same procedure as in the above-described Test Example 3. The amount of each test sample administered was 0.15 mL. In the test, the ranges of PIP joint motion and DIP joint motion were also calculated according to the formula below. Each test was performed using 11 rabbits in Comparative Example 7, 7 rabbits in Examples 7-1 and 7-2, and 8 rabbits in Example 7-3.

Range of PIP joint motion (°)=(flexion angle of PIP joint before application of load)−(flexion angle of PIP joint after application of load)

Range of DIP joint motion (°)=(flexion angle of DIP joint before application of load)−(flexion angle of DIP joint after application of load)    [Numerical formula 2]

Figure 8:
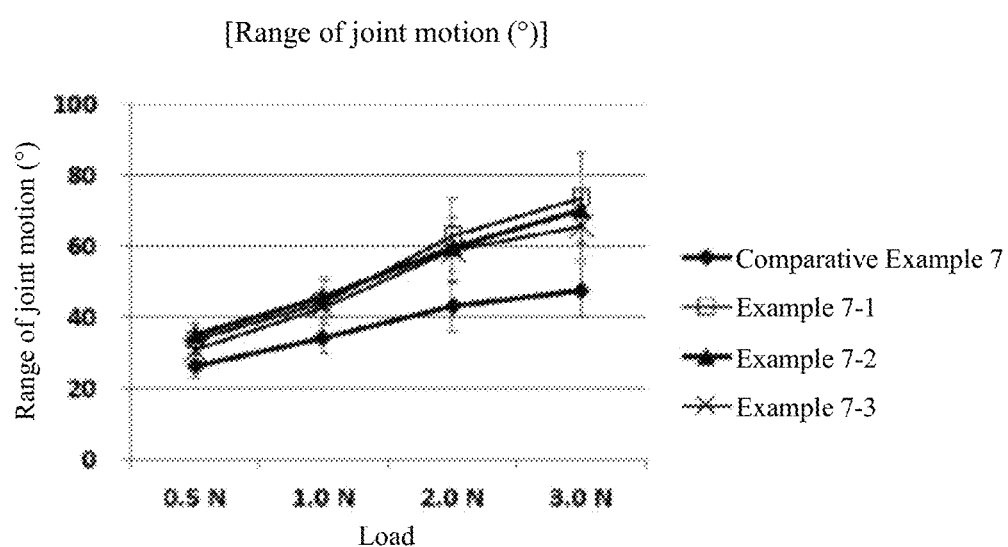
FIG. 8 shows the results of measurement of the range of joint motion in Test Example 7.
Figure 9:
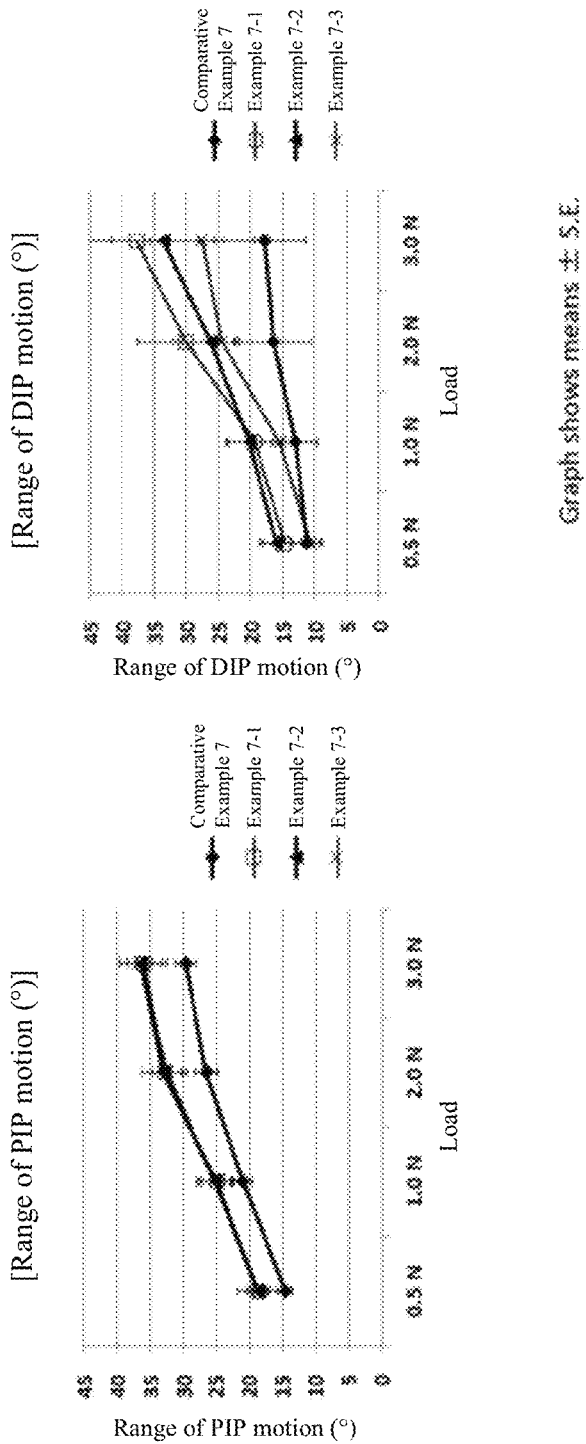
FIG. 9 shows the results of measurement of the ranges of PIP joint motion and DIP joint motion in Test Example 7.
Figure 10:
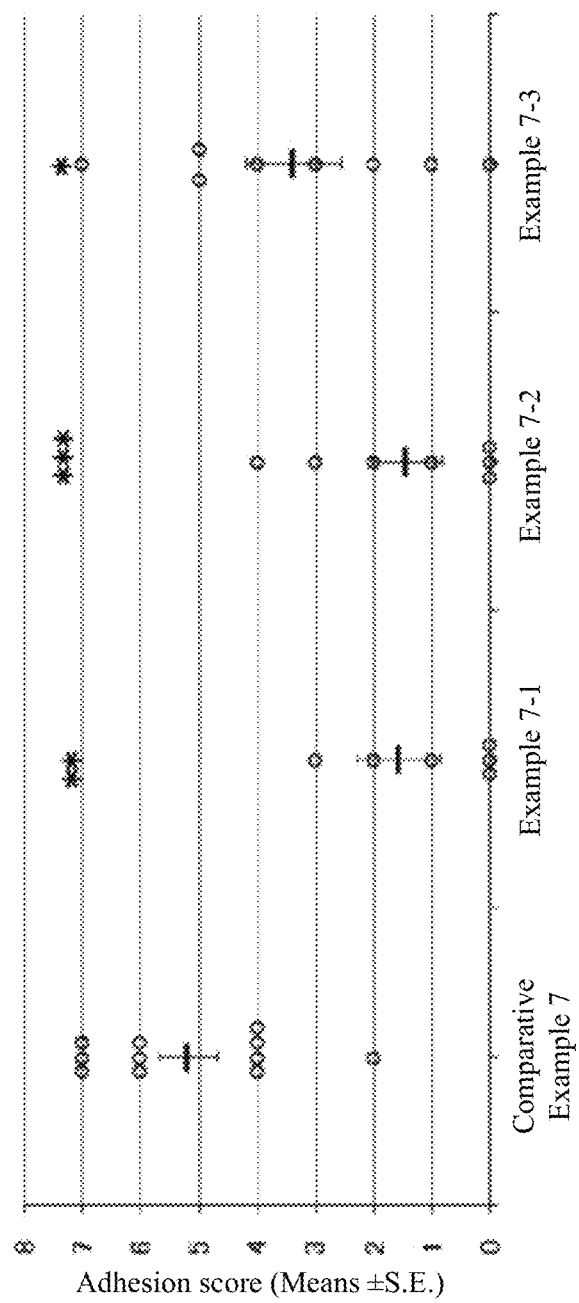
FIG. 10 shows the results of measurement of an adhesion score in Test Example 7.
Figure 11:
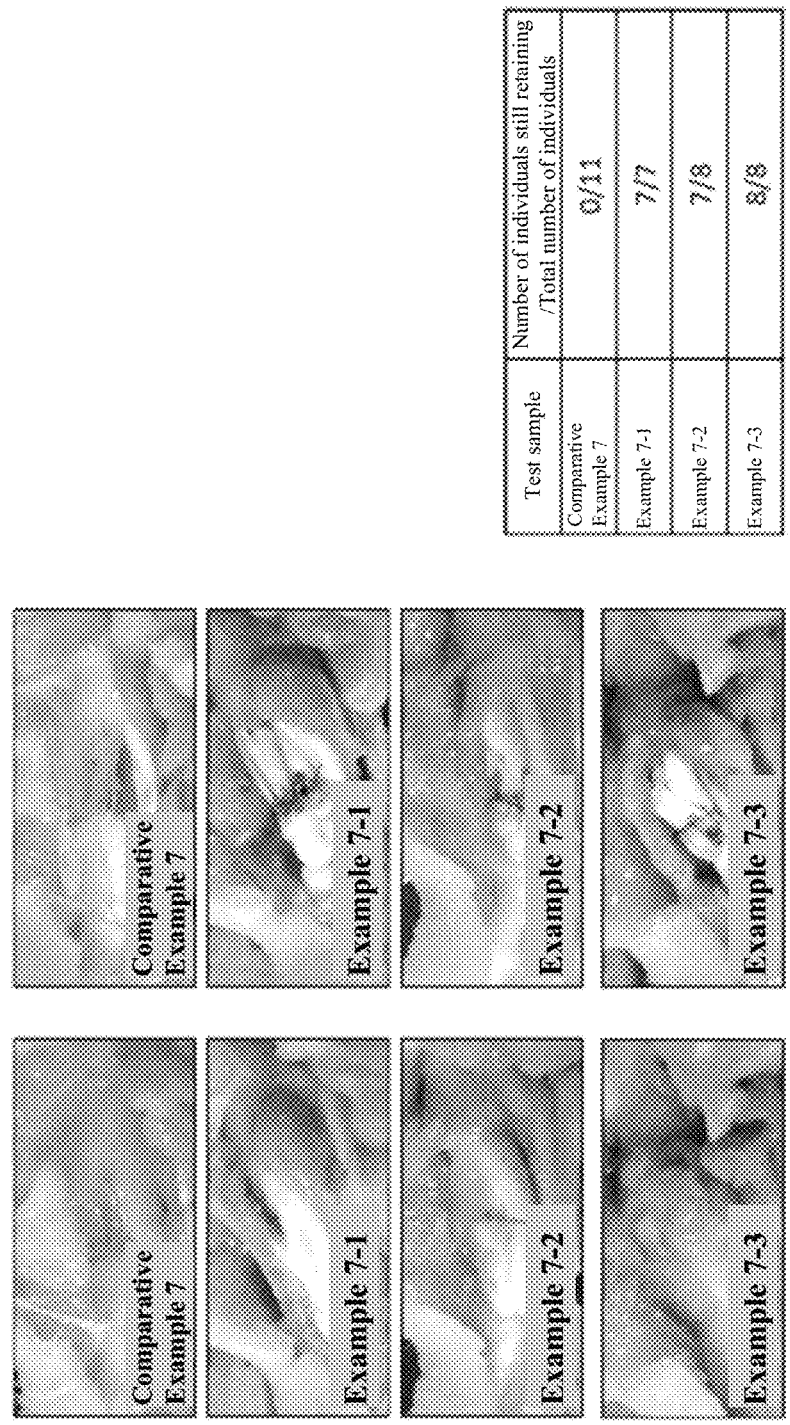
FIG. 11 shows the results of observation on the appearance of a flexor tendon at the end of a test in Test Example 7.
Figure 12:
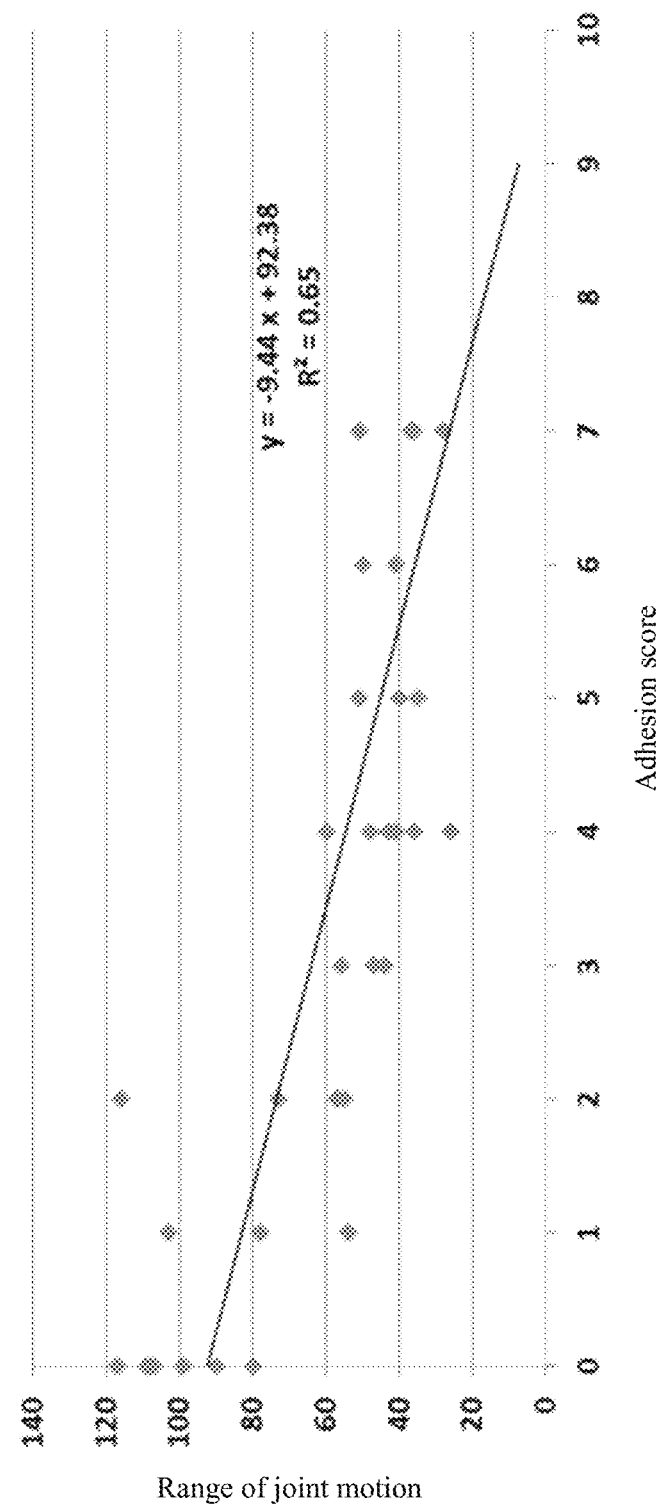
FIG. 12 shows the results of analysis of correlation between the range of joint motion and the adhesion score in Test Example 7.

The results of measurement of the range of joint motion are shown in FIG. 8, the results of measurement of the ranges of PIP joint motion and DIP joint motion are shown in FIG. 9, the results of adhesion scores are shown in FIG. 10, the results of observation of appearance of a flexor tendon at the end of the test are shown in FIG. 11, and the results of analysis of correlation between the range of joint motion and the adhesion score are shown in FIG. 12.

From the results, even when tripeptide 4, oligopeptide 1, and polypeptide 1 having a unit [Gly-Pro-Hyp] were used, antiadhesive effects were observed. However, the antiadhesive effect in polypeptide 1 was lower than those in tripeptide 4 and oligopeptide 1. From these results, it was found that when a peptide containing 5 or less of the unit [Gly-Pro-Hyp] is used, a remarkably excellent antiadhesive effect can be exerted.

Further, as apparent from FIG. 12, a correlation was found between the range of joint motion and the adhesion score. With respect to breaking strength of a sutured flexor digitorum profundus tendon, there was no significant difference between Comparative Example 7 and Examples 7-1 to 7-3.

9. Test Example 8
9-1. Preparation of Test Sample

Test samples having compositions as shown in Table 8 were prepared.

TABLE 8

| Test sample | Composition |
| --- | --- |
| Comparative Example 8 | Physiological saline (Otsuka Pharmaceutical Factory, Inc.) |
| Example 8-1 | Powder composition including tripeptide 4 (45 mg) and crosslinked-gelatin sponge gel powder (B) (30 mg) |

TABLE 8-continued

| Test sample | Composition |
| --- | --- |
| Example 8-2 | Formulation I consisting of tripeptide 4 (powder form), and formulation II containing crosslinked-gelatin sponge gel powder (B) (20% by weight) and physiological saline (hydrogel form) |
| Example 8-3 | Formulation I containing tripeptide 4 (30% by weight) and physiological saline (liquid form), and formulation II containing crosslinked-gelatin sponge gel powder (B) (20% by weight) and physiological saline (hydrogel form) |

9-2. Evaluation of Antiadhesive Effect

An antiadhesive effect was evaluated by the same procedure as in the above-described Test Example 3. Each test sample was administered as follows. In Comparative Example 8, 0.15 mL of the test sample was administered. In Example 8-1, 75 mg of the test sample was administered. In Example 8-2, 45 mg of formulation I was administered, and thereafter 0.15 mL of formulation II was administered. In Example 8-2, 0.075 mL of formulation I and 0.075 mL of formulation II were mixed, and the mixture was administered. In the test, the ranges of PIP joint motion and DIP joint motion were also calculated according to the same procedure as in the above-described Test Example 7.

Figure 13:
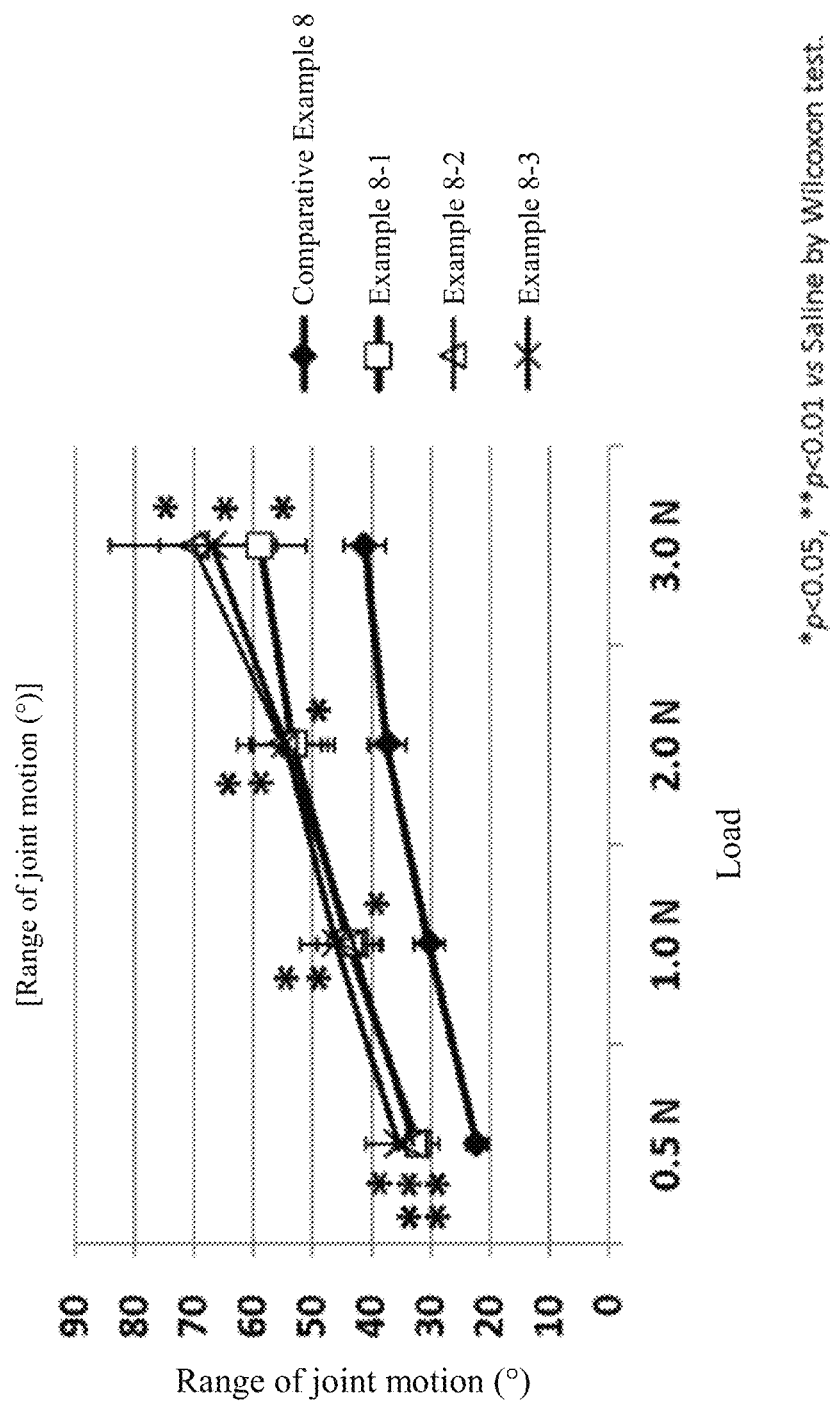
FIG. 13 shows the results of measurement of the range of joint motion in Test Example 8.
Figure 14:
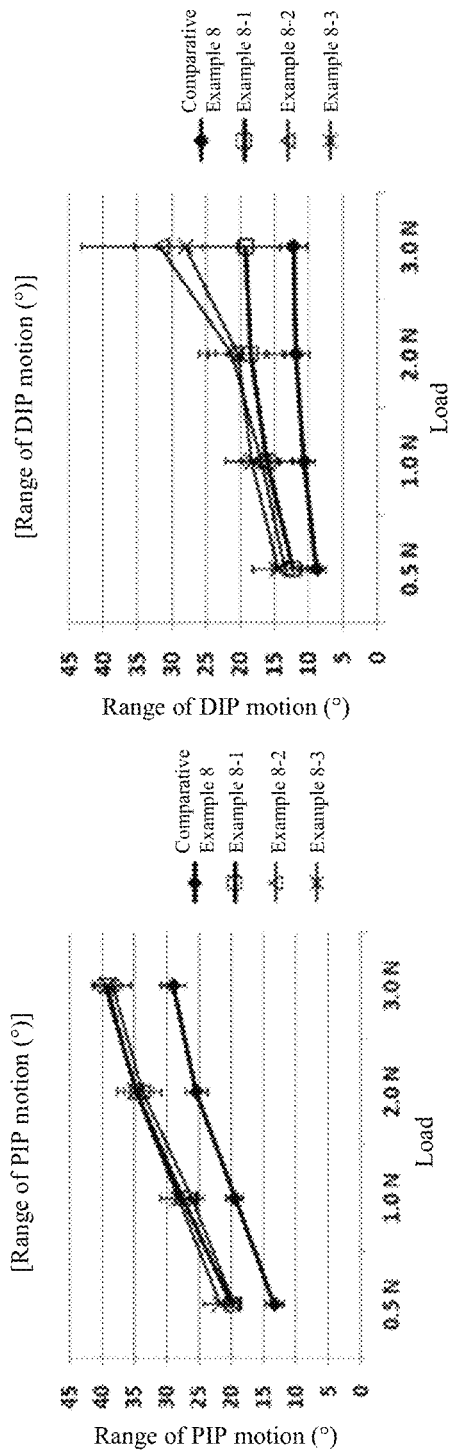
FIG. 14 shows the results of measurement of the ranges of PIP joint motion and DIP joint motion in Test Example 8.
Figure 15:
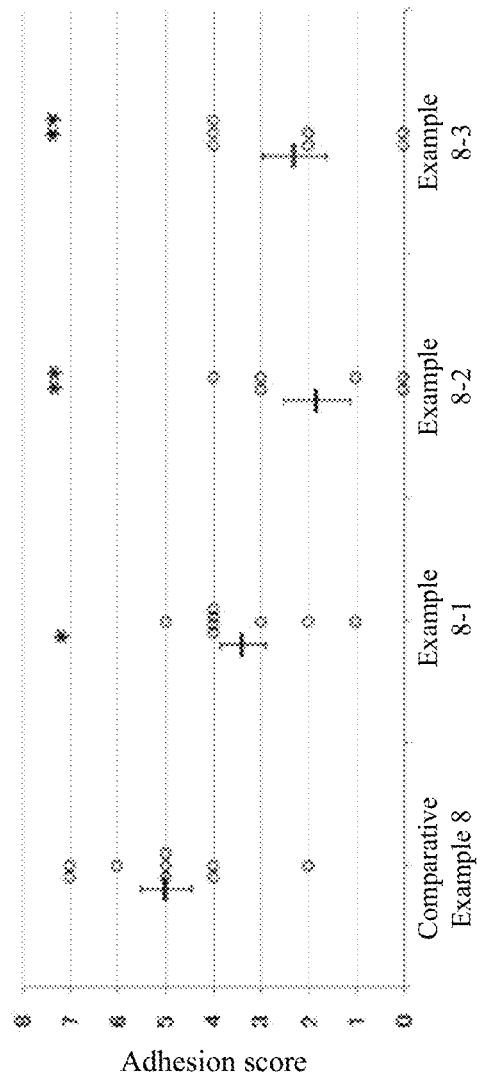
FIG. 15 shows the results of measurement of an adhesion score in Test Example 8.
Figure 16:
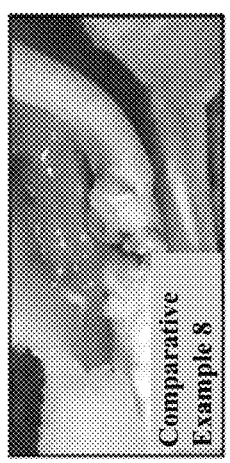
FIG. 16 shows the results of observation on the appearance of a flexor tendon at the end of a test in Test Example 8.
Figure 16:
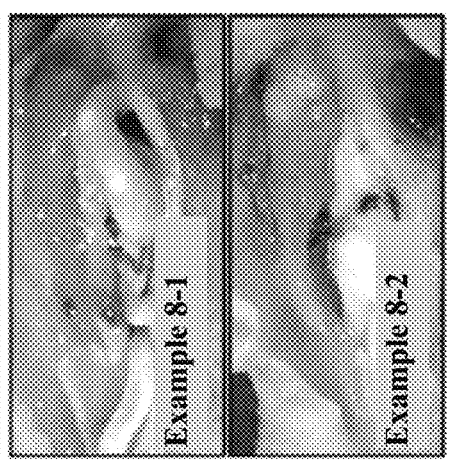
Figure 16:
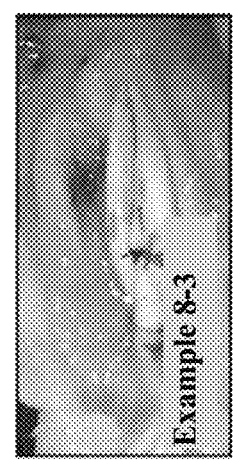
Figure 16:
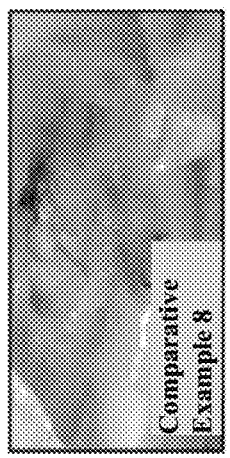
Figure 16:
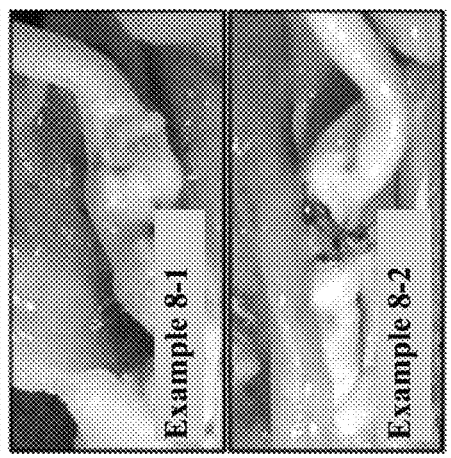
Figure 16:
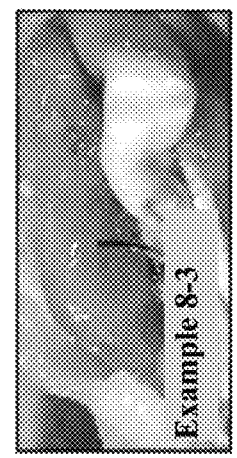
Figure 17:
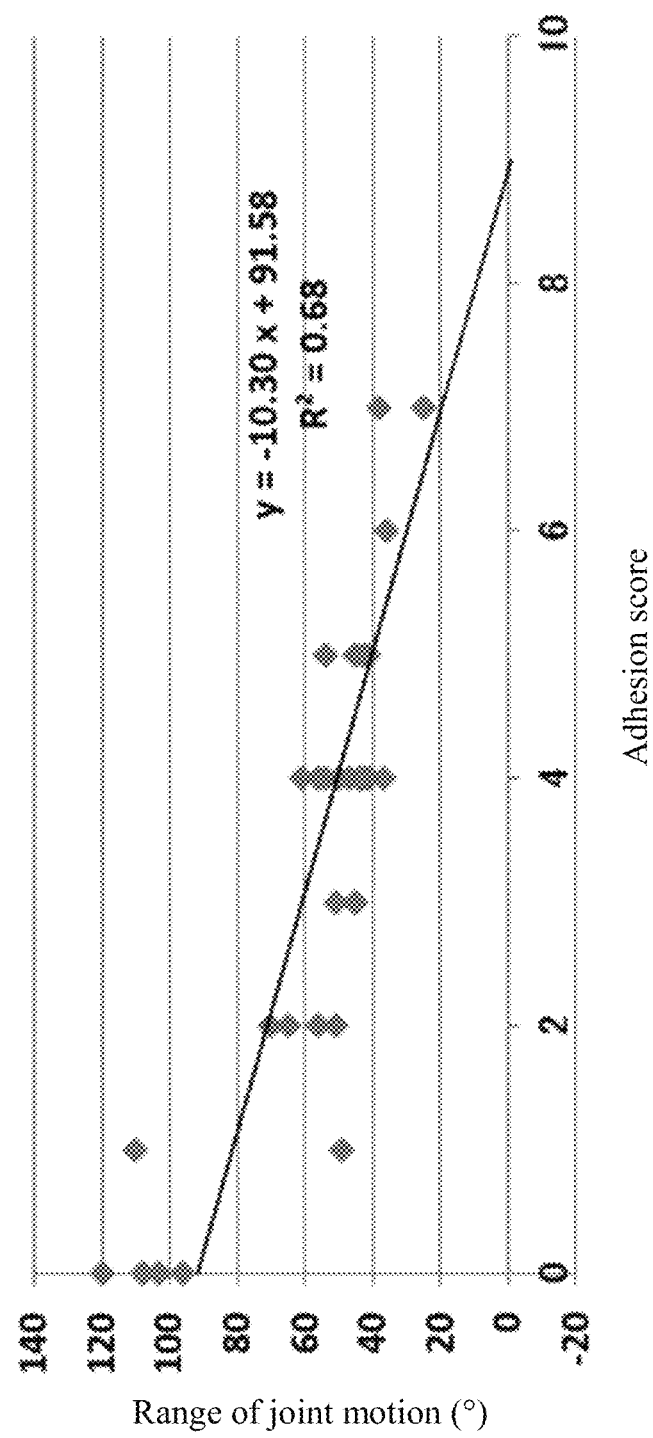
FIG. 17 shows the results of analysis of correlation between the range of joint motion and the adhesion score in Test Example 8.

The results of measurement of the range of joint motion are shown in FIG. 13, the results of measurement of the ranges of PIP joint motion and DIP joint motion are shown in FIG. 14, the results of adhesion scores are shown in FIG. 15, the results of observation of appearance of a flexor tendon at the end of the test are shown in FIG. 16, and the results of analysis of correlation between the range of joint motion and the adhesion score are shown in FIG. 17.

From the results, the combination of tripeptide 4 consisting of Gly-Pro-Hyp and the crosslinked-gelatin sponge gel exerted an antiadhesive effect in any of the following administrations: concurrently administering in mixture powder form (Example 8-1), individually administering the formulation I in powder-form and the formulation II in hydrogel-form (Example 8-2), and concurrently administering in hydrogel form ((Example 8-3). However, in Example 8-1 in which administration was performed in mixture powder form, the range of DIP motion was reduced as compared to those in Examples 8-2 and 8-3.

10. Test Example 9

10-1. Preparation of Test Sample

Test samples having compositions as shown in Table 9 were prepared.

TABLE 9

| Test sample | Composition |
| --- | --- |
| Comparative Example 9 | Physiological saline (Otsuka Pharmaceutical Factory, Inc.) |
| Example 9-1 | Hydrogel composition containing mixture of tripeptide 4 (30% by weight), crosslinked-gelatin sponge gel powder (B) (20% by weight), and physiological saline (50% by weight) |
| Example 9-2 | Hydrogel composition containing mixture of tripeptide 5 (30% by weight), crosslinked-gelatin sponge gel powder (B) (20% by weight), and physiological saline (50% by weight) |

TABLE 9-continued

| Test sample | Composition |
| --- | --- |
| Example 9-3 | Hydrogel composition containing mixture of tripeptide 6 (30% by weight), crosslinked-gelatin sponge gel powder (B) (20% by weight), and physiological saline (50% by weight) |
| Example 9-4 | Hydrogel composition containing mixture of tripeptide 7 (30% by weight), crosslinked-gelatin sponge gel powder (B) (20% by weight), and physiological saline (50% by weight) |
| Example 9-5 | Hydrogel composition containing mixture of tripeptide 8 (30% by weight), crosslinked-gelatin sponge gel powder (B) (20% by weight), and physiological saline (50% by weight) |

10-2. Evaluation of Antiadhesive Effect

An antiadhesive effect was evaluated by the same procedure as in the above-described Test Example 3. The amount of each test sample administered was 0.15 mL. Each test was performed using 9 rabbits in Comparative Example 9 and Example 9-3, 6 rabbits in Example 9-1, and 8 rabbits in Examples 9-2, 9-4, and 9-5.

Figure 18:
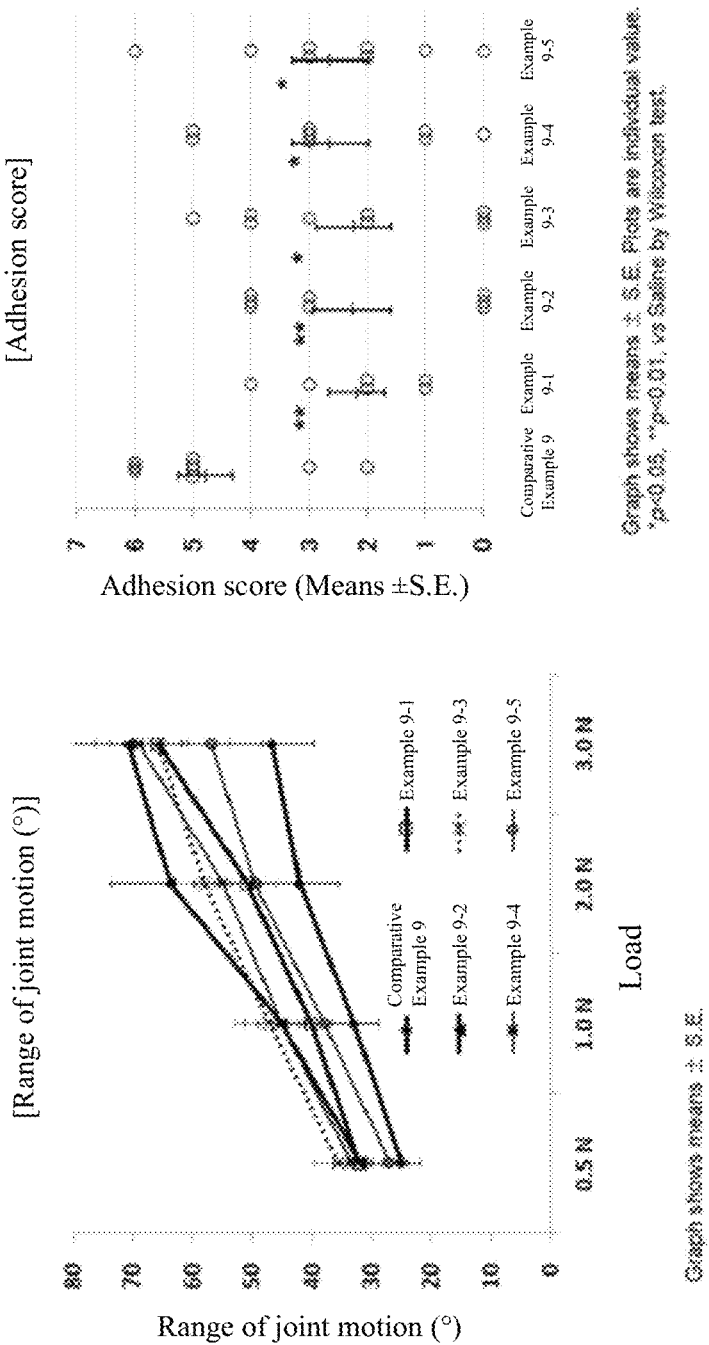
FIG. 18 shows the results of evaluation of an antiadhesive effect in a flexor tendon in Test Example 9.
Figure 19:
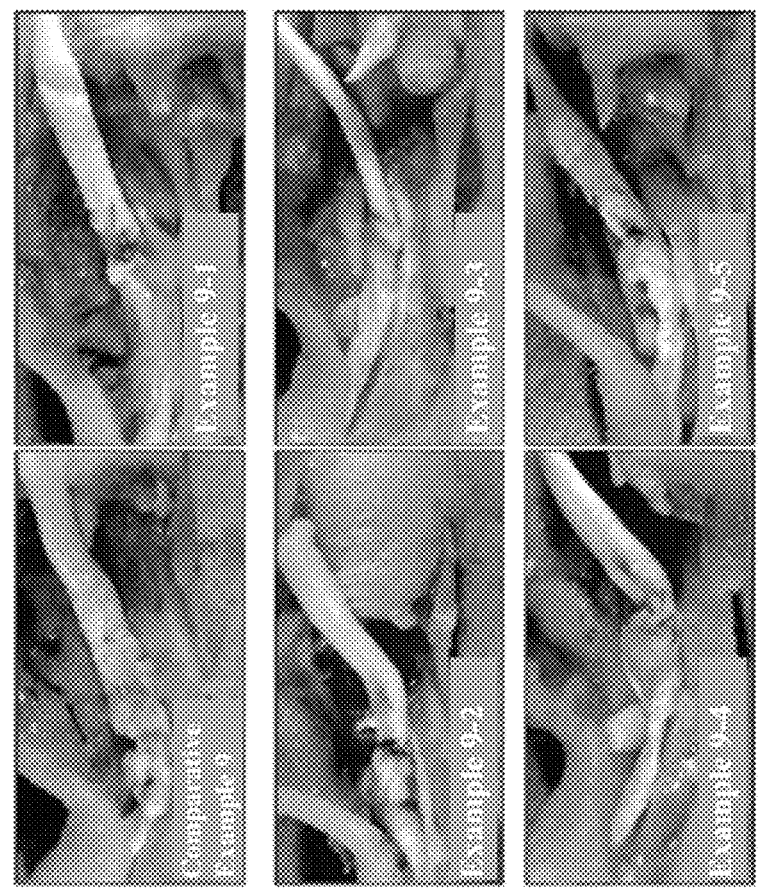
FIG. 19 shows the results of observation on the appearance of a flexor tendon at the end of a test in Test Example 9.

The results of measurements of the range of joint motion and the adhesion score are shown in FIG. 18, and the results of observation of appearance of a flexor tendon at the end of the test are shown in FIG. 19.

From the results, in addition to the case in which tripeptide 4 (Gly-Pro-Hyp) was used, even when tripeptide 5 (Ile-Pro-Hyp), 6 (Asn-Pro-Hyp), 7 (Arg-Pro-Hyp), and 8 (Tyr-Pro-Hyp) were used, antiadhesive effects were observed. That is, from these results, it was confirmed that a tripeptide of "X-Pro-Hyp" (X is any amino acid) can exert an excellent antiadhesive effect when used together with the gelatin gel.

11. Test Example 10

11-1. Preparation of Test Sample

Test samples having compositions as shown in Table 10 were prepared.

TABLE 10

| Test sample | Composition |
| --- | --- |
| Comparative Example 10-1 | Physiological saline (Otsuka Pharmaceutical Factory, Inc.) |
| Example 10 | Hydrogel composition containing mixture of tripeptide 4 (30% by weight), crosslinked-gelatin sponge gel powder (B) (20% by weight), and physiological saline (50% by weight) |
| Comparative Example 10-2 | Hydrogel composition containing mixture of glycine (10% by weight), proline (10% by weight), hydroxyproline (10% by weight), crosslinked-gelatin sponge gel powder (B) (20% by weight), and physiological saline (50% by weight) |

11-2. Evaluation of Antiadhesive Effect

An antiadhesive effect was evaluated by the same procedure as in the above-described Test Example 3. The amount of each test sample administered was 0.15 mL. Each test was performed using 9 rabbits in Comparative Example 10-1, 7 rabbits in Example 10, and 6 rabbits in Comparative Example 10-2.

Figure 20:
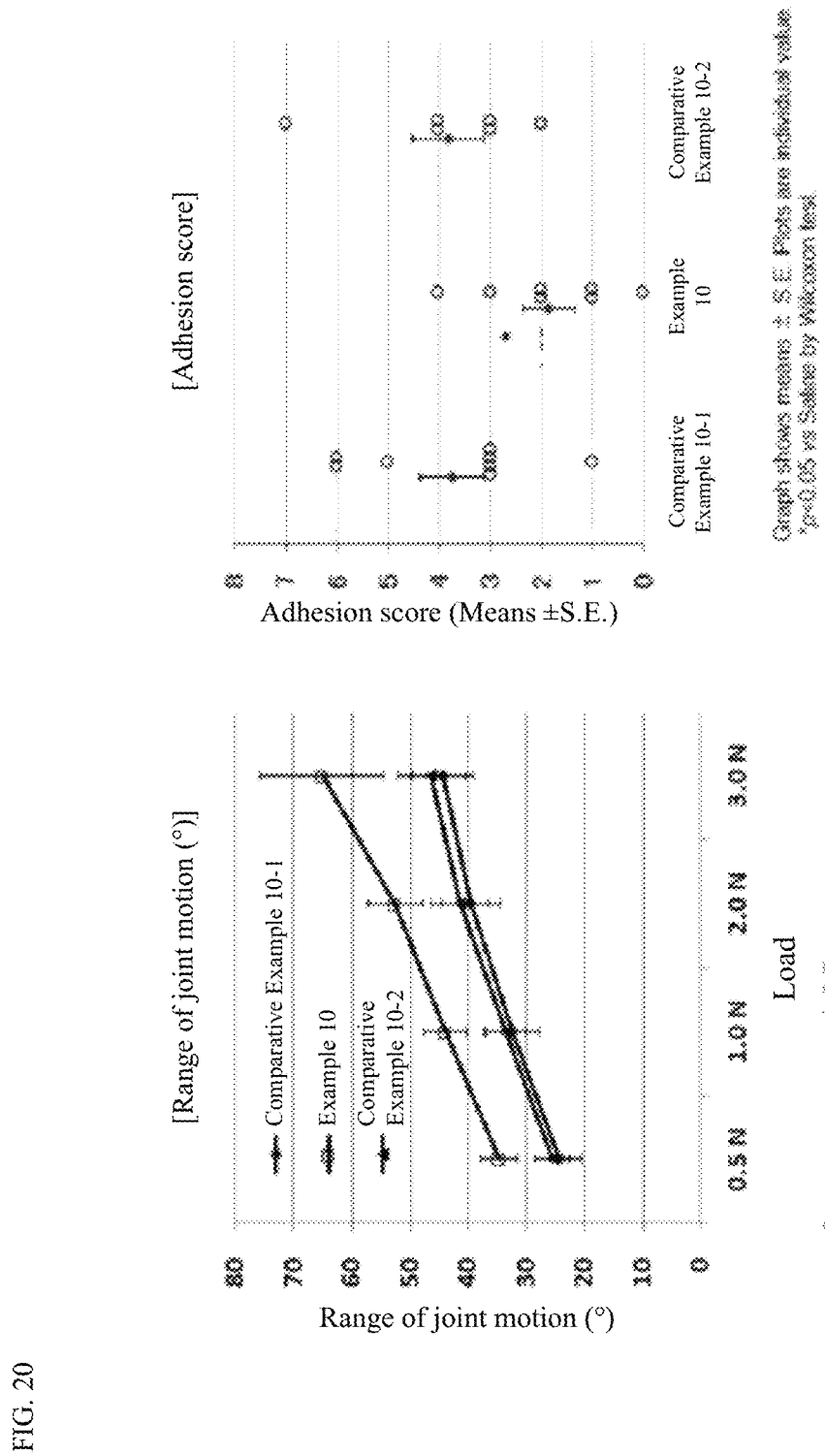
FIG. 20 shows the results of evaluation of an antiadhesive effect in a flexor tendon in Test Example 10.
Figure 21:
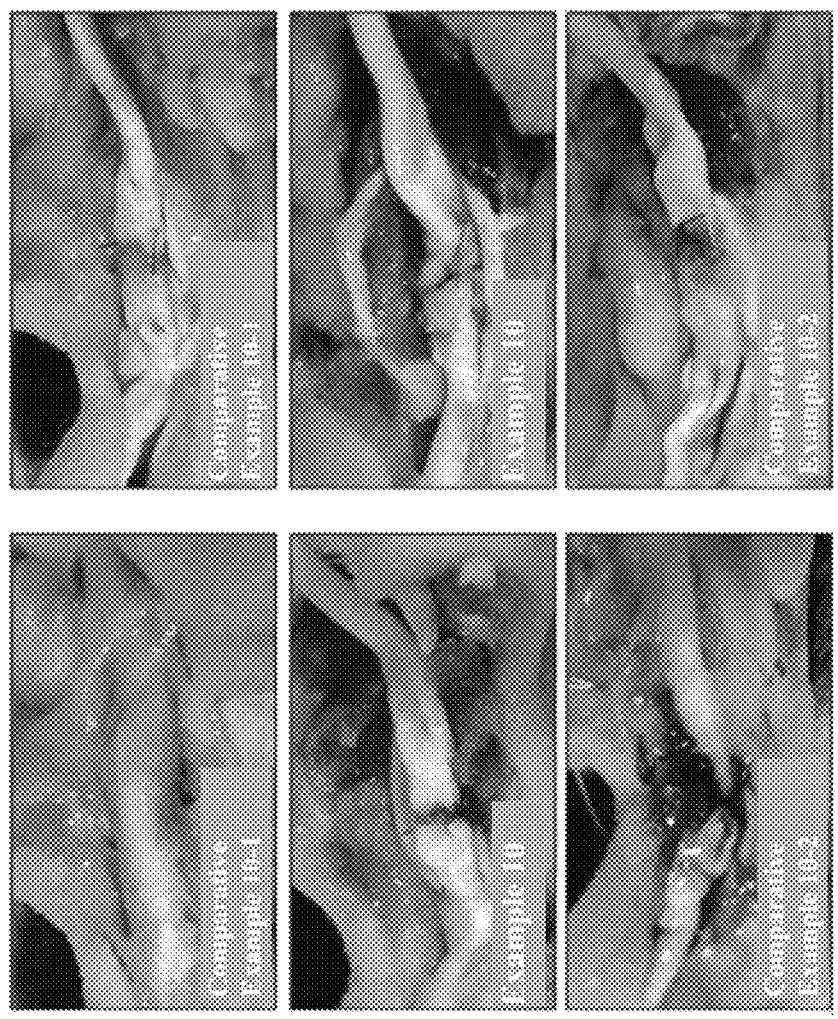
FIG. 21 shows the results of observation on the appearance of a flexor tendon at the end of a test in Test Example 10.

The results of measurements of the range of joint motion and the adhesion score are shown in FIG. 20, and the results of observation of appearance of a flexor tendon at the end of the test are shown in FIG. 21.

From the results, glycine, proline, and hydroxyproline, which are constituent amino acids of tripeptide 4 (Gly-Pro-Hyp), were used as free amino acids together with the gelatin gel, the antiadhesive effect was not observed. That is, from these results, it was found that it is necessary for exerting an antiadhesive effect to use the peptide having a specific sequence in combination with the gelatin gel.

12. Test Example 11

12-1. Preparation of Test Sample

Test samples having compositions as shown in Table 11 were prepared.

TABLE 11

| Test sample | Composition |
| --- | --- |
| Comparative Example 11 | Physiological saline (Otsuka Pharmaceutical Factory, Inc.) |
| Example 11-1 | Hydrogel composition containing mixture of tripeptide 4 (30% by weight), crosslinked-gelatin sponge gel powder (B) (20% by weight), and physiological saline (50 parts by weight) |
| Example 11-2 | Hydrogel composition containing mixture of tripeptide 4 (30% by weight), crosslinked-gelatin sponge gel powder (D) (20% by weight), and physiological saline (50 parts by weight) |

12-2. Evaluation of Antiadhesive Effect

An antiadhesive effect was evaluated by the same procedure as in the above-described Test Example 3. The amount of each test sample administered was 0.15 mL. Each test was performed using 10 rabbits in Comparative Example 11, 9 rabbits in Example 11-1, and 6 rabbits in Example 11-2.

Figure 22:
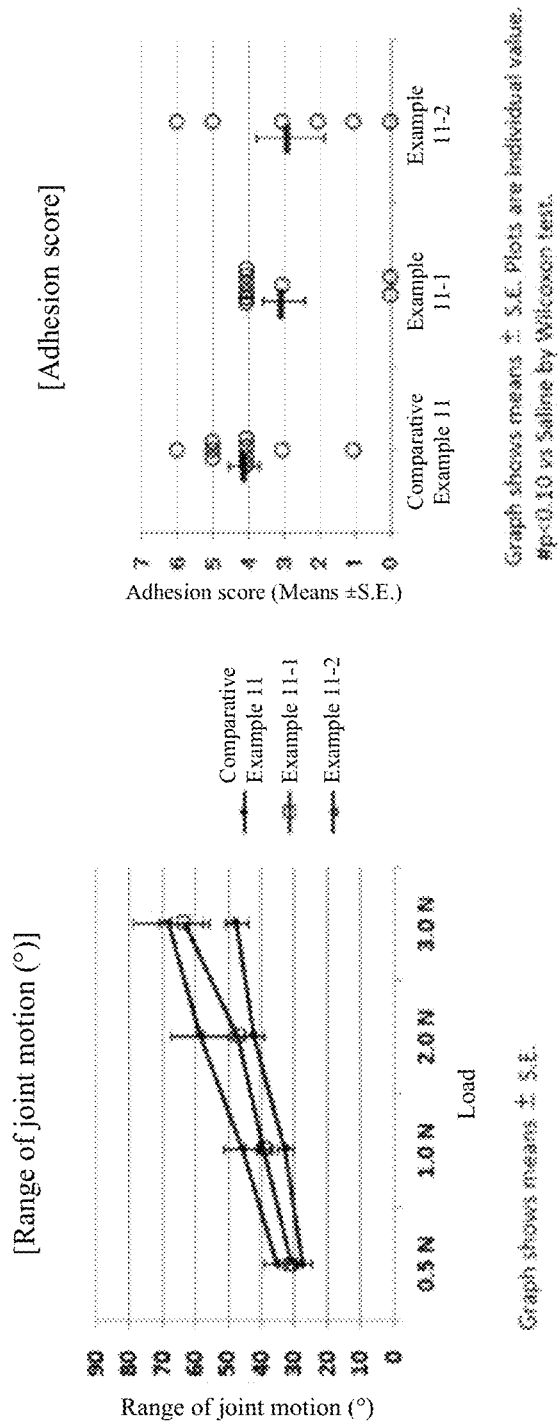
FIG. 22 shows the results of evaluation of an antiadhesive effect in a flexor tendon in Test Example 11.
Figure 23:
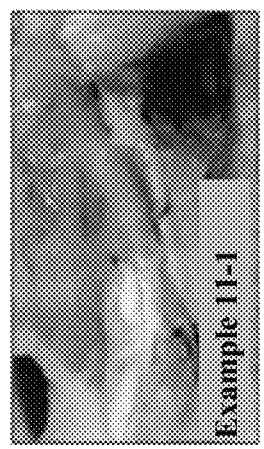
FIG. 23 shows the results of observation on the appearance of a flexor tendon at the end of a test in Test Example 11.
Figure 23:
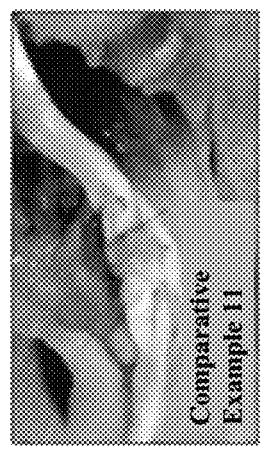
Figure 23:
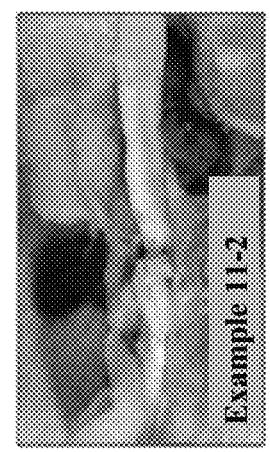

The results of measurements of the range of joint motion and the adhesion score are shown in FIG. 22, and the results of observation of appearance of a flexor tendon at the end of the test are shown in FIG. 23. From the results, it was confirmed that, even when any one of crosslinked-gelatin sponge gel powder (B) and (D) was used, an excellent antiadhesive effect can be exerted by administering together with tripeptide 4 (Gly-Pro-Hyp).

The invention claimed is:

1. An antiadhesive material comprising:
(A) a peptide (A-1) consisting of an amino acid sequence of -(X-Pro-Y)$_n$-, wherein X represents any amino acid, Pro represents proline, Y represents hydroxyproline or proline, and n is an integer of 1 to 10, and/or a peptide (A-2) having an amino acid sequence of -(Pro-Y)$_m$-, wherein Pro represents proline, Y represents hydroxyproline or proline, and m is an integer of 1 to 10; and
(B) a gelatin gel.

2. The antiadhesive material according to claim 1, wherein, in the amino acid sequence (A-1), X is a hydrophobic amino acid, a hydrophilic basic amino acid, or a hydrophilic neutral amino acid.

3. The antiadhesive material according to claim 1, wherein, in the amino acid sequence (A-1), X is glycine, isoleucine, asparagine, arginine, tyrosine, alanine, valine, or leucine.

4. The antiadhesive material according to claim 1, wherein, in the amino acid sequence (A-1), Y is hydroxyproline.

5. The antiadhesive material according to claim 1, wherein, in the amino acid sequence (A-1), X is glycine, isoleucine, asparagine, arginine, or tyrosine, and Y is hydroxyproline.

6. The antiadhesive material according to claim 1, wherein, in the amino acid sequence (A-1), n is an integer of 1 to 5.

7. The antiadhesive material according to claim 1, wherein, in the amino acid sequence (A-2), m is an integer of 1 to 5.

8. The antiadhesive material according to claim 1, wherein the gelatin gel is a crosslinked gelatin gel.

9. The antiadhesive material according to claim 1, wherein the gelatin gel is a gelatin sponge gel.

10. The antiadhesive material according to claim 1, wherein the gelatin gel is a powder-form aerogel or a granule-form hydrogel.

11. The antiadhesive material according to claim 1, wherein the antiadhesive material further comprises an aqueous solvent, and is in hydrogel form containing the peptide and the gelatin gel.

12. The antiadhesive material according to claim 1, wherein the antiadhesive material comprises no aqueous solvent, and is a one-part type which includes a solid formulation containing the peptide and the gelatin gel.

13. The antiadhesive material according to claim 1, wherein the antiadhesive material is a two-part type which includes formulation I containing the peptide and formulation II containing the gelatin gel.

14. The antiadhesive material according to claim 13, wherein the formulation I is in liquid form containing an aqueous solvent, and the formulation II is in hydrogel form containing an aqueous solvent.

15. The antiadhesive material according to claim 13, wherein the formulation I is in liquid form containing an aqueous solvent, and the formulation II is in aerogel form.

16. The antiadhesive material according to claim 13, wherein the formulation I is in powder form, and the formulation II is in hydrogel form containing an aqueous solvent.

17. The antiadhesive material according to claim 13, wherein the formulation I is in powder form, and the formulation II is in aerogel form.

18. A method of manufacturing an antiadhesive material, comprising:
combining formulation I comprising a peptide (A-1) consisting of an amino acid sequence of -(X-Pro-Y)-$_n$, wherein X represents any amino acid, Pro represents proline, Y represents hydroxyproline or proline, and n is an integer of 1 to 5, and/or a peptide (A-2) having an amino acid sequence of -(Pro-Y)$_m$-, wherein Pro represents proline, Y represents hydroxyproline or proline, and m is an integer of 1 to 10; and formulation II comprising a gelatin gel.

19. A method for preventing adhesion, the method comprising administering the antiadhesive material according to claim 1 in an amount effective for preventing adhesion to a site of a biological tissue in need of preventing adhesion.

* * * * *